(12) United States Patent
Quigley et al.

(10) Patent No.: US 12,251,744 B2
(45) Date of Patent: *Mar. 18, 2025

(54) LANDFILL GAS EXTRACTION CONTROL SYSTEM

(71) Applicant: Loci Controls, Inc., Wareham, MA (US)

(72) Inventors: Peter Quigley, Duxbury, MA (US); Ian Martin, Higganum, CT (US); Joseph G. Michels, Pocono Summit, PA (US); Melinda Sims, Seattle, WA (US)

(73) Assignee: Loci Controls, Inc., Wareham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/526,824

(22) Filed: Dec. 1, 2023

(65) Prior Publication Data

US 2024/0109110 A1    Apr. 4, 2024

Related U.S. Application Data

(63) Continuation of application No. 17/167,539, filed on Feb. 4, 2021, now Pat. No. 11,872,610, which is a
(Continued)

(51) Int. Cl.
*B09B 1/00* (2006.01)
*G01N 33/00* (2006.01)
(Continued)

(52) U.S. Cl.
CPC ............... *B09B 1/006* (2013.01); *B09B 1/00* (2013.01); *E21B 43/12* (2013.01); *G01N 1/2294* (2013.01);
(Continued)

(58) Field of Classification Search
CPC .... B09B 1/006; Y02W 30/30; G01N 33/0016
See application file for complete search history.

(56) References Cited

U.S. PATENT DOCUMENTS 3,062,037 A    11/1962   Donner et al.
3,567,387 A     3/1971   Jones
(Continued)

FOREIGN PATENT DOCUMENTS

EP          0 743 515 A1    11/1996
WO    WO 2006/005014 A2     1/2006
(Continued)

OTHER PUBLICATIONS

Campanella et al., Designs for Enhanced Reliability and Calibration of Landfill Gas Measurement and Control Devices. Co-pending U.S. Appl. No. 15/464,236, filed Mar. 20, 2017.
(Continued)

*Primary Examiner* — Janine M Kreck
(74) *Attorney, Agent, or Firm* — Wolf, Greenfield & Sacks, P.C.

(57) ABSTRACT

A control system for controlling extraction of landfill gas from a landfill via a gas extraction system comprising well piping, the landfill gas having a first temperature when extracted, the control system comprising: a gas composition chamber coupled to the well piping and comprising at least one sensor configured to measure one or more characteristics of a landfill gas sample in the gas composition chamber; a temperature control mechanism configured to heat the landfill gas sample in the gas composition chamber to a second temperature at least a threshold amount greater than the first temperature; and a controller configured to control the at least one sensor to measure the one or more characteristics of the landfill gas sample in the gas composition chamber when a temperature of the landfill gas sample in the
(Continued)

gas composition chamber is at least the threshold amount greater than the first temperature.

20 Claims, 13 Drawing Sheets

Related U.S. Application Data continuation of application No. 16/290,387, filed on Mar. 1, 2019, now Pat. No. 10,946,420.

(60) Provisional application No. 62/753,396, filed on Oct. 31, 2018, provisional application No. 62/639,415, filed on Mar. 6, 2018.

(51) Int. Cl.
  *E21B 43/12* (2006.01)
  *G01N 1/22* (2006.01)
  *H05B 3/22* (2006.01)

(52) U.S. Cl.
  CPC ............ *G01N 33/0016* (2013.01); *H05B 3/22* (2013.01); *Y02W 30/30* (2015.05)

(56) References Cited

U.S. PATENT DOCUMENTS

| | | |
|---|---|---|
| 4,026,355 A | 5/1977 | Johnson et al. |
| 4,191,541 A | 3/1980 | Jenkins |
| 4,226,675 A | 10/1980 | Lewis et al. |
| 4,227,897 A | 10/1980 | Reed |
| 4,494,380 A | 1/1985 | Cross |
| 4,499,378 A | 2/1985 | Miyatake et al. |
| 4,670,148 A | 6/1987 | Schneider |
| 4,890,672 A | 1/1990 | Hall |
| 5,063,519 A | 11/1991 | Zison |
| 5,209,941 A | 5/1993 | Wuest |
| 5,223,229 A | 6/1993 | Brucker |
| 5,239,861 A | 8/1993 | Fujita et al. |
| 5,451,249 A | 9/1995 | Spiegel et al. |
| 5,458,006 A | 10/1995 | Roqueta |
| 5,665,314 A | 9/1997 | Berger et al. |
| 5,681,360 A | 10/1997 | Siwajek et al. |
| 5,695,641 A | 12/1997 | Cosulich et al. |
| 5,830,262 A | 11/1998 | Marchini et al. |
| 6,169,962 B1 | 1/2001 | Brookshire et al. |
| 6,196,324 B1 | 3/2001 | Giacomino et al. |
| 6,231,153 B1 | 5/2001 | Elgee |
| 6,241,950 B1 | 6/2001 | Veelenturf et al. |
| 6,399,391 B1 | 6/2002 | Tomlin |
| 6,497,804 B1 | 12/2002 | Gorfinkel et al. |
| 6,591,695 B1 | 7/2003 | Brookshire et al. |
| 6,595,287 B2 | 7/2003 | Fisher |
| 6,611,760 B2 | 8/2003 | Bentley et al. |
| 6,749,368 B2 | 6/2004 | Ankeny et al. |
| 6,799,477 B2 | 10/2004 | Brookshire et al. |
| 6,999,883 B1 | 2/2006 | Brady et al. |
| 7,187,299 B2 | 3/2007 | Kunerth et al. |
| 7,198,433 B2 | 4/2007 | Augenstein et al. |
| 7,243,730 B2 | 7/2007 | Casey |
| 7,273,098 B2 | 9/2007 | Evans et al. |
| 7,373,976 B2 | 5/2008 | Casey |
| 7,387,163 B2 | 6/2008 | Seegers et al. |
| 7,448,828 B2 | 11/2008 | Augenstein et al. |
| 7,748,450 B2 | 7/2010 | Mundell |
| 7,866,921 B2 | 1/2011 | Stamoulis |
| 7,950,464 B2 | 5/2011 | Atencio et al. |
| 7,972,082 B2 | 7/2011 | Augenstein et al. |
| 8,047,276 B2 | 11/2011 | Stamoulis |
| 8,163,242 B2 | 4/2012 | Elkins |
| 8,168,121 B2 | 5/2012 | Elkins |
| 8,186,211 B2 | 5/2012 | Boult et al. |
| 8,840,708 B1 | 9/2014 | Morrow et al. |
| 8,924,029 B2 | 12/2014 | Nath et al. |
| 8,927,909 B2 | 1/2015 | Le Neel et al. |
| 8,944,014 B2 | 2/2015 | Cutlip et al. |
| 9,062,536 B2 | 6/2015 | Fischer et al. |
| 10,029,290 B2 | 7/2018 | Campanella et al. |
| 10,042,402 B2 | 8/2018 | Eremenko et al. |
| 10,400,560 B2 | 9/2019 | Campanella et al. |
| 10,408,747 B2 | 9/2019 | Schlueter et al. |
| 10,449,578 B2 | 10/2019 | Campanella et al. |
| 10,556,259 B2 | 2/2020 | Campanella et al. |
| 10,576,514 B2 | 3/2020 | Campanella et al. |
| 10,576,515 B2 | 3/2020 | Campanella et al. |
| 10,639,687 B2 | 5/2020 | Campanella et al. |
| 10,682,678 B2 | 6/2020 | Campanella et al. |
| 10,705,063 B2 | 7/2020 | Campanella et al. |
| 10,882,086 B2 | 1/2021 | Quigley et al. |
| 10,946,420 B2 * | 3/2021 | Quigley .................. B09B 1/006 |
| 11,007,555 B2 | 5/2021 | Campanella et al. |
| 11,067,549 B2 | 7/2021 | Campanella et al. |
| 11,072,006 B2 | 7/2021 | Campanella et al. |
| 11,084,074 B2 | 8/2021 | Campanella et al. |
| 11,235,361 B2 | 2/2022 | Quigley et al. |
| 11,273,473 B2 | 3/2022 | Quigley et al. |
| 11,484,919 B2 | 11/2022 | Quigley et al. |
| 11,486,573 B1 | 11/2022 | Siegel |
| 11,491,521 B2 | 11/2022 | Quigley et al. |
| 11,602,777 B2 | 3/2023 | Campanella et al. |
| 11,602,778 B2 | 3/2023 | Campanella et al. |
| 11,623,256 B2 | 4/2023 | Quigley et al. |
| 11,845,115 B2 | 12/2023 | Campanella et al. |
| 11,850,639 B2 | 12/2023 | Campanella et al. |
| 11,865,594 B2 | 1/2024 | Quigley et al. |
| 11,872,610 B2 * | 1/2024 | Quigley .................. B09B 1/006 |
| 11,883,864 B2 | 1/2024 | Quigley et al. |
| 11,885,784 B2 | 1/2024 | Campanella et al. |
| 11,977,062 B2 | 5/2024 | Campanella et al. |
| 2001/0005812 A1 | 6/2001 | Brookshire et al. |
| 2002/0101718 A1 | 8/2002 | Negishi |
| 2003/0000281 A1 | 1/2003 | Ketler et al. |
| 2003/0046975 A1 | 3/2003 | Wewers et al. |
| 2004/0055359 A1 | 3/2004 | Ketler et al. |
| 2004/0121201 A1 | 6/2004 | Roche et al. |
| 2006/0034664 A1 | 2/2006 | Augenstein et al. |
| 2006/0251540 A1 | 11/2006 | Benning et al. |
| 2007/0224085 A1 | 9/2007 | Tooley |
| 2007/0225923 A1 | 9/2007 | Tooley |
| 2007/0254196 A1 | 11/2007 | Richards et al. |
| 2008/0011248 A1 | 1/2008 | Cutlip et al. |
| 2008/0127726 A1 | 6/2008 | Elkins |
| 2009/0136298 A1 | 5/2009 | Augenstein et al. |
| 2010/0006281 A1 | 1/2010 | DuBrucq |
| 2010/0310733 A1 | 12/2010 | Hoffman |
| 2011/0061439 A1 | 3/2011 | Dong et al. |
| 2011/0061874 A1 | 3/2011 | Stamoulis |
| 2011/0081586 A1 | 4/2011 | McAlister |
| 2011/0132104 A1 | 6/2011 | Benson et al. |
| 2011/0198094 A1 | 8/2011 | Stamoulis |
| 2011/0231099 A1 | 9/2011 | Elkins |
| 2011/0272420 A1 | 11/2011 | Landess et al. |
| 2012/0191349 A1 | 7/2012 | Lenz et al. |
| 2012/0206715 A1 | 8/2012 | Laub |
| 2012/0287418 A1 | 11/2012 | Scherer et al. |
| 2013/0036811 A1 | 2/2013 | Boult |
| 2013/0180703 A1 | 7/2013 | Colby |
| 2013/0193325 A1 | 8/2013 | Phillips et al. |
| 2013/0247647 A1 | 9/2013 | Mahoney et al. |
| 2013/0334418 A1 | 12/2013 | Cowie et al. |
| 2014/0023576 A1 | 1/2014 | Yezerets et al. |
| 2014/0182846 A1 | 7/2014 | Fischer et al. |
| 2014/0284935 A1 | 9/2014 | Disbennett et al. |
| 2014/0338878 A1 | 11/2014 | Tessnow |
| 2015/0000426 A1 | 1/2015 | Mustang |
| 2015/0168274 A1 | 6/2015 | Sheffield |
| 2015/0226045 A1 | 8/2015 | Fischer et al. |
| 2015/0275632 A1 | 10/2015 | Fischer et al. |
| 2015/0330938 A1 | 11/2015 | Henson et al. |
| 2015/0354032 A1 | 12/2015 | Yuan et al. |
| 2015/0362468 A1 | 12/2015 | Gerhold |
| 2016/0011159 A1 | 1/2016 | Sekiya et al. |
| 2016/0025365 A1 | 1/2016 | Moudy |

(56) References Cited

U.S. PATENT DOCUMENTS

| | | |
|---|---|---|
| 2016/0025696 A1 | 1/2016 | Birks et al. |
| 2016/0033391 A1 | 2/2016 | Stroganov et al. |
| 2016/0123946 A1 | 5/2016 | Dufresne |
| 2016/0169826 A1 | 6/2016 | Youssi et al. |
| 2016/0209133 A1 | 7/2016 | Hu et al. |
| 2016/0237007 A1 | 8/2016 | Morrow et al. |
| 2016/0238494 A1 | 8/2016 | Chrin, II |
| 2016/0247183 A1 | 8/2016 | Foody |
| 2016/0287870 A1 | 10/2016 | Yip et al. |
| 2016/0377457 A1 | 12/2016 | Zhang et al. |
| 2017/0080762 A1 | 3/2017 | Guinart et al. |
| 2017/0122065 A1 | 5/2017 | Fischer et al. |
| 2017/0173505 A1 | 6/2017 | Dhingra et al. |
| 2017/0176590 A1 | 6/2017 | Sharonov et al. |
| 2017/0216891 A1 | 8/2017 | Campanella et al. |
| 2017/0216892 A1 | 8/2017 | Campanella et al. |
| 2017/0216893 A1 | 8/2017 | Campanella et al. |
| 2017/0218730 A1 | 8/2017 | Campanella et al. |
| 2017/0218731 A1 | 8/2017 | Campanella et al. |
| 2017/0218732 A1 | 8/2017 | Campanella et al. |
| 2017/0254196 A1 | 9/2017 | Campanella et al. |
| 2017/0254787 A1 | 9/2017 | Campanella et al. |
| 2017/0328750 A1 | 11/2017 | Jehle et al. |
| 2018/0003572 A1 | 1/2018 | Garsd et al. |
| 2018/0003684 A1 | 1/2018 | Kerr |
| 2018/0024202 A1 | 1/2018 | Erickson et al. |
| 2018/0154408 A1 | 6/2018 | Ko et al. |
| 2018/0164137 A1 | 6/2018 | Layher et al. |
| 2018/0171604 A1 | 6/2018 | Kim et al. |
| 2018/0209248 A1 | 7/2018 | Patel et al. |
| 2018/0304323 A1 | 10/2018 | Campanella et al. |
| 2019/0069245 A1 | 2/2019 | Miller et al. |
| 2019/0232346 A1 | 8/2019 | Speer et al. |
| 2019/0277119 A1 | 9/2019 | Campion |
| 2019/0277821 A1 | 9/2019 | Quigley et al. |
| 2020/0086365 A1 | 3/2020 | Campanella et al. |
| 2020/0101504 A1 | 4/2020 | Quigley et al. |
| 2020/0101505 A1 | 4/2020 | Quigley et al. |
| 2020/0130033 A1 | 4/2020 | Campanella et al. |
| 2020/0197990 A1 | 6/2020 | Quigley et al. |
| 2020/0254497 A1 | 8/2020 | Campanella et al. |
| 2020/0306806 A1 | 10/2020 | Quigley et al. |
| 2020/0306807 A1 | 10/2020 | Quigley et al. |
| 2021/0046524 A1 | 2/2021 | Quigley et al. |
| 2021/0178436 A1 | 6/2021 | Quigley et al. |
| 2021/0229142 A1 | 7/2021 | Quigley et al. |
| 2021/0372977 A1 | 12/2021 | Campanella et al. |
| 2022/0008970 A1 | 1/2022 | Quigley et al. |
| 2022/0008971 A1 | 1/2022 | Quigley et al. |
| 2022/0008972 A1 | 1/2022 | Quigley et al. |
| 2022/0008973 A1 | 1/2022 | Quigley et al. |
| 2022/0062959 A1 | 3/2022 | Campanella et al. |
| 2022/0062960 A1 | 3/2022 | Campanella et al. |
| 2023/0114970 A1 | 4/2023 | Quigley et al. |
| 2023/0234112 A1 | 7/2023 | Campanella et al. |
| 2023/0271234 A1 | 8/2023 | Campanella et al. |
| 2023/0302508 A1 | 9/2023 | Campanella et al. |
| 2023/0302509 A1 | 9/2023 | Campanella et al. |
| 2023/0324353 A1 | 10/2023 | Campanella et al. |
| 2024/0017311 A1 | 1/2024 | Campanella et al. |
| 2024/0066572 A1 | 2/2024 | Campanella et al. |
| 2024/0066573 A1 | 2/2024 | Campanella et al. |
| 2024/0100578 A1 | 3/2024 | Campanella et al. |
| 2024/0109111 A1 | 4/2024 | Campanella et al. |
| 2024/0167990 A1 | 5/2024 | Campanella et al. |

FOREIGN PATENT DOCUMENTS

| | | |
|---|---|---|
| WO | WO 2015/072989 A1 | 5/2015 |
| WO | WO 2016/010985 A1 | 1/2016 |
| WO | WO 2018/194650 A1 | 10/2018 |
| WO | WO 2020/072457 A1 | 4/2020 |

OTHER PUBLICATIONS

Campanella et al., Designs for Enhanced Reliability and Calibration of Landfill Gas Measurement and Control Devices. Co-pending U.S. Appl. No. 15/478,583, filed Apr. 4, 2017.

Campanella et al., Designs for Enhanced Reliability and Calibration of Landfill Gas Measurement and Control Devices. Co-pending U.S. Appl. No. 17/343,317, filed Jun. 9, 2021.

Campanella et al., Designs for Enhanced Reliability and Calibration of Landfill Gas Measurement and Control Devices. Co-pending U.S. Appl. No. 18/327,580, filed Jun. 1, 2023.

Campanella et al., Designs for Enhanced Reliability and Calibration of Landfill Gas Measurement and Control Devices. Co-pending U.S. Appl. No. 18/425,421, filed Jan. 29, 2024.

Campanella et al., Devices and Techniques Relating to Landfill Gas Extraction. Co-pending U.S. Appl. No. 14/532,807, filed Nov. 4, 2014.

Campanella et al., Devices and Techniques Relating to Landfill Gas Extraction. Co-pending U.S. Appl. No. 15/456,936, filed Mar. 13, 2017.

Campanella et al., Devices and Techniques Relating to Landfill Gas Extraction. Co-pending U.S. Appl. No. 15/456,982, filed Mar. 13, 2017.

Campanella et al., Devices and Techniques Relating to Landfill Gas Extraction. Co-pending U.S. Appl. No. 15/493,174, filed Apr. 21, 2017.

Campanella et al., Devices and Techniques Relating to Landfill Gas Extraction. Co-pending U.S. Appl. No. 15/493,184, filed Apr. 21, 2017.

Campanella et al., Devices and Techniques Relating to Landfill Gas Extraction. Co-pending U.S. Appl. No. 15/493,201, filed Apr. 21, 2017.

Campanella et al., Devices and Techniques Relating to Landfill Gas Extraction. Co-pending U.S. Appl. No. 16/024,085, filed Jun. 29, 2018.

Campanella et al., Devices and Techniques Relating to Landfill Gas Extraction. Co-pending U.S. Appl. No. 16/694,745, filed Nov. 25, 2019.

Campanella et al., Devices and Techniques Relating to Landfill Gas Extraction. Co-pending U.S. Appl. No. 16/726,232, filed Dec. 23, 2019.

Campanella et al., Devices and Techniques Relating to Landfill Gas Extraction. Co-pending U.S. Appl. No. 16/745,892, filed Jan. 17, 2020.

Campanella et al., Devices and Techniques Relating to Landfill Gas Extraction. Co-pending U.S. Appl. No. 16/831,131, filed Mar. 26, 2020.

Campanella et al., Devices and Techniques Relating to Landfill Gas Extraction. Co-pending U.S. Appl. No. 17/369,318, filed Jul. 7, 2021.

Campanella et al., Devices and Techniques Relating to Landfill Gas Extraction. Co-pending U.S. Appl. No. 17/369,395, filed Jul. 7, 2021.

Campanella et al., Devices and Techniques Relating to Landfill Gas Extraction. Co-pending U.S. Appl. No. 18/158,742, filed Jan. 24, 2023.

Campanella et al., Devices and Techniques Relating to Landfill Gas Extraction. Co-pending U.S. Appl. No. 18/168,983, filed Feb. 14, 2023.

Campanella et al., Devices and Techniques Relating to Landfill Gas Extraction. Co-pending U.S. Appl. No. 18/327,638, filed Jun. 1, 2023.

Campanella et al., Devices and Techniques Relating to Landfill Gas Extraction. Co-pending U.S. Appl. No. 18/327,694, filed Jun. 1, 2023.

Quigley et al., Automated Compliance Measurement and Control for Landfill Gas Extraction Systems. Co-pending U.S. Appl. No. 17/152,252, filed Jan. 19, 2021.

Quigley et al., Automated Compliance Measurement and Control for Landfill Gas Extraction Systems. Co-pending U.S. Appl. No. 18/540,281, filed Dec. 14, 2023.

Quigley et al., Devices and Techniques Relating to Landfill Gas Extraction. Co-pending U.S. Appl. No. 16/927,471, filed Jul. 13, 2020.

(56) References Cited

OTHER PUBLICATIONS

Quigley et al., Devices and Techniques Relating to Landfill Gas Extraction. Co-pending U.S. Appl. No. 16/927,479, filed Jul. 13, 2020.
Quigley et al., Devices and Techniques Relating to Landfill Gas Extraction. Co-pending U.S. Appl. No. 16/927,482, filed Jul. 13, 2020.
Quigley et al., Devices and Techniques Relating to Landfill Gas Extraction. Co-pending U.S. Appl. No. 16/927,488, filed Jul. 13, 2020.
Quigley et al., Landfill Gas Extraction Control System. Co-pending U.S. Appl. No. 16/290,387, filed Mar. 1, 2019.
Quigley et al., Landfill Gas Extraction Control System. Co-pending U.S. Appl. No. 17/167,539, filed Feb. 4, 2021.
Quigley et al., Landfill Gas Extraction Systems and Methods. Co-pending U.S. Appl. No. 16/589,372, filed Oct. 1, 2019.
Quigley et al., Landfill Gas Extraction Systems and Methods. Co-pending U.S. Appl. No. 16/589,391, filed Oct. 1, 2019.
Quigley et al., Landfill Gas Extraction Systems and Methods. Co-pending U.S. Appl. No. 16/901,405, filed Jun. 15, 2020.
Quigley et al., Landfill Gas Extraction Systems and Methods. Co-pending U.S. Appl. No. 16/901,430, filed Jun. 15, 2020.
Quigley et al., Landfill Gas Extraction Systems and Methods. Co-pending U.S. Appl. No. 17/086,987, filed Nov. 2, 2020.
Quigley et al., Landfill Gas Extraction Systems and Methods. Co-pending U.S. Appl. No. 17/959,446, filed Oct. 4, 2022.
[No Author Listed], 40 CFR Parts 51, 52, and 60. US Code of Federal Regulations. Mar. 12, 1996; 61(49):9905-44. https://www.govinfo.gov/content/pkg/FR-1996-03-12/pdf/96-5529.pdf (Last accessed Jun. 25, 2024).
Extended European Search Report for European Application No. 24154125.9 dated Apr. 30, 2024.
U.S. Appl. No. 14/532,807, Campanella et al., filed Nov. 4, 2014.
U.S. Appl. No. 15/456,936, Campanella et al., filed Mar. 13, 2017.
U.S. Appl. No. 15/456,982, Campanella et al., filed Mar. 13, 2017.
U.S. Appl. No. 15/464,236, Campanella et al., filed Mar. 20, 2017.
U.S. Appl. No. 15/478,583, Campanella et al., filed Apr. 4, 2017.
U.S. Appl. No. 15/493,174, Campanella et al., filed Apr. 21, 2017.
U.S. Appl. No. 15/493,184, Campanella et al., filed Apr. 21, 2017.
U.S. Appl. No. 15/493,201, Campanella et al., filed Apr. 21, 2017.
U.S. Appl. No. 16/024,085, Campanella et al., filed Jun. 29, 2018.
U.S. Appl. No. 16/290,387, Quigley et al., filed Mar. 2, 2019.
U.S. Appl. No. 16/589,372, Quigley et al., filed Oct. 1, 2019.
U.S. Appl. No. 16/589,391, Quigley et al., filed Oct. 1, 2019.
U.S. Appl. No. 16/694,745, Campanella et al., filed Nov. 25, 2019.
U.S. Appl. No. 16/726,232, Campanella et al., filed Dec. 23, 2019.
U.S. Appl. No. 16/745,892, Campanella et al., filed Jan. 17, 2020.
U.S. Appl. No. 16/831,131, Campanella et al., filed Mar. 26, 2020.
U.S. Appl. No. 16/901,405, Quigley et al., filed Jun. 15, 2020.
U.S. Appl. No. 16/901,430, Quigley et al., filed Jun. 15, 2020.
U.S. Appl. No. 16/927,471, Quigley et al., filed Jul. 13, 2020.
U.S. Appl. No. 16/927,479, Quigley et al., filed Jul. 13, 2020.
U.S. Appl. No. 16/927,482, Quigley et al., filed Jul. 13, 2020.
U.S. Appl. No. 16/927,488, Quigley et al., filed Jul. 13, 2020.
U.S. Appl. No. 17/086,987, Quigley et al., filed Nov. 2, 2020.
U.S. Appl. No. 17/152,252, Quigley et al., filed Jan. 19, 2021.
U.S. Appl. No. 17/167,539, Quigley et al., filed Feb. 4, 2021.
U.S. Appl. No. 17/343,317, Campanella et al., filed Jun. 9, 2021.
U.S. Appl. No. 17/369,395, Campanella et al., filed Jul. 7, 2021.
U.S. Appl. No. 17/369,318, Campanella et al., filed Jul. 7, 2021.
U.S. Appl. No. 17/959,446, Quigley et al., filed Oct. 4, 2022.
U.S. Appl. No. 18/158,742, Campanella et al., filed Jan. 24, 2023.
U.S. Appl. No. 18/168,983, Campanella et al., filed Feb. 14, 2023.
U.S. Appl. No. 18/327,516, Campanella et al., filed Jun. 1, 2023.
U.S. Appl. No. 18/132,753, Quigley et al., filed Apr. 10, 2023.
U.S. Appl. No. 18/327,580, Campanella et al., filed Jun. 1, 2023.
U.S. Appl. No. 18/327,638, Campanella et al., filed Jun. 1, 2023.
U.S. Appl. No. 18/327,694, Campanella et al., filed Jun. 1, 2023.
U.S. Appl. No. 18/498,770, Campanella et al., filed Oct. 31, 2023.
U.S. Appl. No. 18/498,869, Campanella et al., filed Oct. 31, 2023.
International Search Report and Written Opinion for International Application No. PCT/US2017/020196 mailed Jun. 7, 2017.
Invitation to Pay Additional Fees for International Application No. PCT/US17/28818 mailed Jul. 10, 2017.
International Search Report and Written Opinion for International Application No. PCT/US17/28818 mailed Sep. 8, 2017.
International Search Report and Written Opinion for International Application No. PCT/US2019/020251 mailed May 31, 2019.
Extended European Search Report for European Application No. 17760717.3 dated Oct. 2, 2019.
International Search Report and Written Opinion for International Application No. PCT/US2019/054013 mailed Dec. 4, 2019.
Extended European Search Report for European Application No. 17906368.0 dated Oct. 15, 2020.
International Preliminary Report on Patentability for International Application No. PCT/US2019/054013 mailed Apr. 15, 2021.
International Search Report and Written Opinion for International Application No. PCT/US2021/013850 mailed Jun. 21, 2021.
International Search Report and Written Opinion for International Application No. PCT/US2021/040653 mailed Nov. 26, 2021.
Communication pursuant to Article 94(3) EPC for European Application No. 17760717.3 dated Feb. 21, 2022.
Extended European Search Report for European Application No. 19869105.7 dated May 23, 2022.
Communication pursuant to Article 94(3) EPC for European Application No. 17906368.0 dated Aug. 4, 2022.
International Preliminary Report on Patentability for International Application No. PCT/US2021/013850 mailed Aug. 11, 2022.
International Preliminary Report on Patentability for International Application No. PCT/US2021/040653 mailed Jan. 26, 2023.
Communication pursuant to Article 94(3) EPC for European Application No. 17906368.0 dated May 11, 2023.
Communication pursuant to Article 94(3) EPC for European Application No. 21705025.1 dated Feb. 15, 2024.
Quigley et al., Devices and Techniques Relating to Landfill Gas Extraction. Co-pending U.S. Appl. No. 18/132,753, filed Apr. 10, 2023.
Campanella et al., Devices and Techniques Relating to Landfill Gas Extraction. Co-pending U.S. Appl. No. 18/327,516, filed Jun. 1, 2023.
Campanella et al., Devices and Techniques Relating to Landfill Gas Extraction. Co-pending U.S. Appl. No. 18/498,770, filed Oct. 31, 2023.
Campanella et al., Devices and Techniques Relating to Landfill Gas Extraction. Co-pending U.S. Appl. No. 18/498,869, filed Oct. 31, 2023.
[No Author Listed], 40 CFR 60.755. US Code of Federal Regulations. Jul. 2017:243-45. https://www.govinfo.gov/content/pkg/CFR-2017-title40-vol8/pdf/CFR-2017-title40-vol8-sec60-755.pdf.
[No Author Listed], 50% CH4, 35% CO2, 15% N2. Instrument Depot. 2015. http://www.instrumentdepot.com/50-methane-35-carbon-dioxide-15-nitrogen-c-1_27_472.html.
[No Author Listed], Cloud-Based Wellwatcher Analytics Platform Offers 24/7/365 Visibility on Landfill Gas-Collection Systems. Tech Note. Loci Controls. Nov. 2016. 1 page.
[No Author Listed], Increase Landfill Gas Collection By Up To 30%. Tech Note. Loci Controls. Oct. 2016. 1 page.
[No Author Listed], Loci Controller Combines Active Flow Control With 24/7/365 Real-Time Gas-Composition Analysis to Maximize Landfill Gas Extraction. Tech Note. Loci Controls. Nov. 2016. 1 page.
[No Author Listed], Loci Sentry Utilizes Passive Flow and Gas-Composition Monitoring in Conjunction With Loci Controller and Wellwatcher Analytics to Maximize Landfill Gas Collection. Tech Note. Loci Controls. Nov. 2016. 1 page.
[No Author Listed], Methacontrol® Optimizing landfill gas recovery. Oct. 9, 2013. http://www.veolia.com/en/veolia-group/media/news/methacontrol-r. 1 page.
Bieker et al., Real-Time Production Optimization of Offshore Oil and Gas Production Systems: A Technology Survey. SPE International. 2006. 8 pages.
Bingham et al., Automated Landfill Gas Collection Increases Landfill Gas Flow and Quality at Oklahoma City Landfill. Loci Controls.

(56) References Cited

OTHER PUBLICATIONS

Mar. 7, 2018. 14 pages. https://locicontrols.com/perch/resources/aria-white-paper-022119-1.pdf [Last accessed Nov. 10, 2022].

Collins et al., Web-based monitoring of year-length deployments of autonomous gas sensing platforms on landfill sites. 2011 IEEE Sensors Proceedings. 2011:1620-3.

Fay et al., Remote Real-Time Monitoring of Subsurface Landfill Gas Migration. Sensors. 2011;11(7):6603-29.

Xu et al., Impact of changes in barometric pressure on landfill methane emission. AGU Publications. Jul. 10, 2014. 17 pages.

\* cited by examiner

LANDFILL GAS EXTRACTION CONTROL SYSTEM

CROSS-REFERENCE TO RELATED APPLICATIONS

This application is a continuation of and claims priority under 35 U.S.C. § 120 to U.S. patent application Ser. No. 17/167,539, titled "LANDFILL GAS EXTRACTION CONTROL SYSTEM", filed Feb. 4, 2021, which is a continuation of and claims priority under 35 U.S.C. § 120 to U.S. patent application Ser. No. 16/290,387, titled "LANDFILL GAS EXTRACTION CONTROL SYSTEM", filed Mar. 1, 2019, which claims the benefit under § 119(e) of U.S. Provisional Application Ser. No. 62/639,415 titled "LANDFILL GAS EXTRACTION CONTROL SYSTEM" and filed on Mar. 6, 2018, and U.S. Provisional Application Ser. No. 62/753,396 titled "SYSTEMS AND METHODS FOR HEATING LANDFILL GAS WELL PIPING" and filed on Oct. 31, 2018, each of which is incorporated by reference herein in its entirety.

FEDERALLY SPONSORED RESEARCH

This invention was made with government support under SBIR Phase II Award No. 1632439, awarded by the National Science Foundation. The government has certain rights in the invention.

BACKGROUND

Landfills produce gas as a result of decomposition of organic waste in the landfill. The decomposition process may result in release of methane and other gases. Landfill sites are often capped with a layer of cover material (e.g., called a "cap") to prevent escape of the released gases. Landfills may further install gas extraction systems to pull landfill gas out before it can penetrate the cover layer and escape. The gas extraction systems may comprise multiple wells drilled into the landfill, and landfill gas may be extracted from the landfill via the wells into a gas collection system. The extracted landfill gas may be used to generate electricity, put in a pipeline for distribution, or disposed of.

SUMMARY

Some embodiments provide for a control system for controlling extraction of landfill gas from a landfill via a gas extraction system, the landfill gas having a first temperature when extracted, the gas extraction system comprising at least one vacuum source, well piping, and at least one well coupled to the at least one vacuum source through the well piping. The control system comprises: a gas composition chamber coupled to the well piping and comprising at least one sensor configured to measure one or more characteristics of a landfill gas sample in the gas composition chamber; a temperature control mechanism configured to heat the landfill gas sample in the gas composition chamber to a second temperature at least a threshold amount greater than the first temperature; and a controller configured to control the at least one sensor to measure the one or more characteristics of the landfill gas sample in the gas composition chamber when a temperature of the landfill gas sample in the gas composition chamber is at least the threshold amount greater than the first temperature.

According to one embodiment, the second temperature is at least one degree Celsius greater than the first temperature of the landfill gas. According to one embodiment, the controller is further configured to maintain the temperature of the landfill gas sample in the gas composition chamber at a constant temperature greater than or equal to the second temperature. According to one embodiment, the controller is configured to maintain the temperature of the landfill gas at 55 degrees Celsius. According to one embodiment, the controller comprises a PID controller.

According to one embodiment, the gas composition chamber further comprises a first temperature sensor configured to measure a temperature of the landfill gas sample in the gas composition chamber. According to one embodiment, the control system further comprises a second temperature sensor configured to measure the first temperature, the second temperature sensor being different from the first temperature sensor.

According to one embodiment, the temperature control mechanism comprises a heating element, and wherein the heating element is in the gas composition chamber. According to one embodiment, the temperature control mechanism comprises a heating element, wherein the heating element is outside of the gas composition chamber. According to one embodiment, the heating element comprises a resistive surface configured to generate heat as a result of electrical current flowing through the resistive surface.

According to one embodiment, the gas composition chamber comprises a conductive material. According to one embodiment, the gas composition chamber comprises a polymer. According to one embodiment, the gas composition chamber comprises a thermoplastic. According to one embodiment, the conductive material comprises a heat conductive metal.

According to one embodiment, the gas composition chamber comprises an insulation material. According to one embodiment, the insulation material comprises foam. According to one embodiment, the insulation material comprises aerogel.

According to one embodiment, the control system further comprises a condenser configured to: condense water vapor in the landfill gas sample into liquid water prior to the landfill gas sample entering the gas composition chamber; and remove the liquid water.

Some embodiments provide for a method for controlling extraction of landfill gas from a landfill through a gas extraction system, wherein the landfill gas has a first temperature when extracted. The method comprises: obtaining a sample of landfill gas in a gas composition chamber; heating the landfill gas sample in the gas composition chamber to a second temperature at least a threshold amount greater than the first temperature; and controlling at least one sensor to measure one or more characteristics of the landfill gas sample in the gas composition chamber when a temperature of the landfill gas sample in the gas composition chamber is at least the threshold amount greater than the first temperature.

According to one embodiment, the gas extraction system comprises at least one flow control mechanism, and the method further comprises controlling the at least one flow control mechanism based on the measured one or more characteristics of the landfill gas sample in the gas composition chamber. According to one embodiment, the second temperature is at least one degree Celsius greater than the first temperature.

According to one embodiment, the method further comprises maintaining the temperature of the landfill gas sample in the gas composition chamber at a constant temperature greater than or equal to the second temperature. According to one embodiment, the method further comprises maintaining the temperature of the landfill gas sample in the gas composition chamber at 55 degrees Celsius.

According to one embodiment, measuring the one or more characteristics of the landfill gas sample comprises measuring a concentration of methane in the landfill gas sample in the gas composition chamber. According to one embodiment, measuring the one or more characteristics of the landfill gas sample comprises measuring a concentration of oxygen in the landfill gas sample in the gas composition chamber. According to one embodiment, the method further comprises determining a measure of energy content of landfill gas being extracted from the landfill based on the measured concentration of methane.

According to one embodiment, the gas extraction system comprises at least one flow control mechanism, and the method further comprises controlling the at least one flow control mechanism of the gas extraction system based on the measured energy content. According to one embodiment, controlling the at least one flow control mechanism based on the measured energy content comprises: determining whether the measured energy content is different from a target energy content; and when it is determined that the measured energy content is different from the target energy content, automatically controlling the at least one flow control mechanism to change energy content of the landfill gas being extracted from the landfill.

According to one embodiment, the method further comprises heating the landfill gas sample in the gas composition chamber by heating a surface of the gas composition chamber.

Some embodiments provide for a control system for controlling extraction of landfill gas from a landfill through a gas extraction system, wherein the landfill gas has a first temperature when extracted. The system comprises at least one computer hardware processor and at least one non-transitory computer-readable storage medium that, when executed by the at least one computer hardware processor, causes the at least one computer hardware processor to perform a method comprising: obtaining a sample of landfill gas in a gas composition chamber; heating the landfill gas sample in the gas composition chamber to a second temperature at least a threshold amount greater than the first temperature; and controlling at least one sensor to measure one or more characteristics of the landfill gas sample in the gas composition chamber when a temperature of the landfill gas sample in the gas composition chamber is at least the threshold amount greater than the first temperature.

According to one embodiment, the first temperature is greater than a temperature of the landfill gas when extracted from the landfill. According to one embodiment, the first temperature is approximately equal to a temperature of the landfill gas when extracted from the landfill.

Some embodiments provide for at least one non-transitory computer-readable storage medium that, when executed by at least one computer hardware processor, causes the at least one computer hardware processor to perform a method for controlling extraction of landfill gas from a landfill through a gas extraction system, wherein the landfill gas has a first temperature when extracted. The method comprises: obtaining a sample of landfill gas in a gas composition chamber; heating the landfill gas sample in the gas composition chamber to a second temperature at least a threshold amount greater than the first temperature; and controlling at least one sensor to measure one or more characteristics of the landfill gas sample in the gas composition chamber when a temperature of the landfill gas sample in the gas composition chamber is at least the threshold amount greater than the first temperature.

Some embodiments provide for a control system for controlling extraction of landfill gas from a landfill via a gas extraction system, the gas extraction system comprising at least one vacuum source, well piping, and at least one well coupled to the at least one vacuum source through the well piping. The control system comprises: a gas composition chamber coupled to the well piping and comprising at least one sensor configured to measure one or more characteristics of a landfill gas sample in the gas composition chamber; a temperature control mechanism configured to maintain a temperature of the landfill gas sample in the gas composition chamber at a first temperature; and a controller configured to control the at least one sensor to measure the one or more characteristics of the landfill gas sample in the gas composition chamber when the temperature of the landfill gas sample in the gas composition chamber is at the first temperature.

Some embodiments provide for a system for controlling extraction of landfill gas from a landfill via a gas extraction system, the gas extraction system comprising a vacuum source, well piping, and a well coupled to the vacuum source through the well piping. The system comprises: a temperature sensor for measuring a temperature of a portion of the well piping, the portion of the well piping disposed between the well and a control system for controlling a flow of landfill gas through the well piping; a heating device for heating the portion of the well piping; and a controller configured to: obtain, from the temperature sensor, a first temperature of the portion of the well piping; and in response to determining that the first temperature is less than a first threshold temperature, control the heating device to heat the portion of the well piping.

According to one embodiment, wherein the heating device comprises a resistive heating element. According to one embodiment, the heating device comprises a polyimide. According to one embodiment, the controller is configured to control the heating device at least in part by controlling an electrical current applied to the heating device.

According to one embodiment, the controller is further configured to control the heating device at least in part by turning the heating device on or off. According to one embodiment, the controller is further configured to: in response to determining that the first temperature is greater than a second threshold temperature, control the heating device to stop heating the portion of the well piping.

According to one embodiment, the control system comprises an automatically controlled valve for controlling flow of landfill gas through the well piping. According to one embodiment, the control system further comprises a conductor configured to distribute heat generated by the heating device through the portion of the well piping. According to one embodiment, the conductor comprises heat tape adhered to the portion of the well piping. According to one embodiment, the conductor comprises a metallic conductor.

According to one embodiment, the control system further comprises insulation for insulating the portion of the well piping. According to one embodiment, the insulation comprises an insulative jacket covering the portion of the well piping. According to one embodiment, the insulation comprises pour-in foam. According to one embodiment, the portion of the well piping comprises a first pipe, and the system further comprises a second pipe around at least a portion of the first pipe. According to one embodiment, the insulation is disposed in at least a portion of a space between the second pipe and the at least a portion of the first pipe.

According to one embodiment, the well piping includes a manually controlled valve for controlling a flow of landfill gas, and the system further comprises insulation for insulating the valve. According to one embodiment, the control system further comprises a box around an enclosure of the valve, wherein the insulation is disposed in at least a portion of a space between the box and the enclosure of the valve.

According to one embodiment, the heating device comprises a battery for powering the heating device. According to one embodiment, the heating device comprises a solar panel for charging the battery.

According to one embodiment, the controller is remote from the well piping. According to one embodiment, the control system further comprises a transmitter configured to transmit the first temperature to the controller. According to one embodiment, the transmitter is further configured to transmit diagnostic information. According to one embodiment, the heating device further comprises a receiver configured to receive at least one control input from the controller.

Some embodiments provide a method of controlling extraction of landfill gas from a landfill through a gas extraction system. The method comprises: obtaining, from a temperature sensor, a first temperature of a portion of well piping that couples a gas extraction well of the landfill to a vacuum source, the portion of the well piping disposed between the gas extraction well and a control system for controlling a flow of landfill gas through the well piping; determining whether the first temperature is less than a first threshold temperature; and in response to determining that the first temperature is less than the first threshold temperature, controlling a heating device to heat the portion of the well piping.

According to one embodiment, the first threshold temperature is 0 degrees Celsius. According to one embodiment, controlling the heating device to heat the portion of the well piping comprises turning on the heating device.

According to one embodiment, the method further comprises: determining whether the first temperature is greater than a second threshold temperature that is greater than the first threshold temperature; and in response to determining that the first temperature is greater than the second threshold temperature, controlling the heating device to stop heating the portion of the well piping. According to one embodiment, controlling the heating device to heat the portion of the well piping comprises controlling an electrical current that flows through the heating device.

According to one embodiment, the method further comprises adhering heat tape to the portion of the well piping for distributing heat generated by the heating device. According to one embodiment, the method further comprises insulating the portion of the well piping.

According to one embodiment, the portion of the well piping comprises a first pipe and insulating the portion of the well piping comprises: installing a second pipe around at least a portion of the first pipe; and disposing insulation in at least a portion of a space between the second pipe and the at least a portion of the first pipe. According to one embodiment, the well piping includes a valve for controlling a flow of landfill gas and the method further comprises: installing a box around an enclosure of the valve; and disposing insulation in at least a portion of a space between the box and the enclosure of the valve.

According to one embodiment, the method further comprises installing a conductor outside of the portion of the well piping for distributing heat through the portion of the well piping. According to one embodiment, the method further comprises charging a battery for powering the heating device using a solar panel.

Some embodiments provide for a control system for controlling extraction of landfill gas from a landfill via a gas extraction system, the gas extraction system comprising a vacuum source, well piping, and a well coupled to the vacuum source through the well piping, the control system comprising: a controller configured to: receive, from a temperature sensor, a temperature of a portion of the well piping, the portion of the well piping disposed between the well and a control system for controlling a flow of landfill gas through the well piping; determine whether the temperature is less than a first threshold temperature; and in response to determining that the first temperature is less than the first threshold temperature, controlling a heating device to heat the portion of the well piping.

BRIEF DESCRIPTION OF DRAWINGS

Various aspects and embodiments will be described with reference to the following figures. It should be appreciated that the figures are not necessarily drawn to scale.

DETAILED DESCRIPTION

Figure 1A:
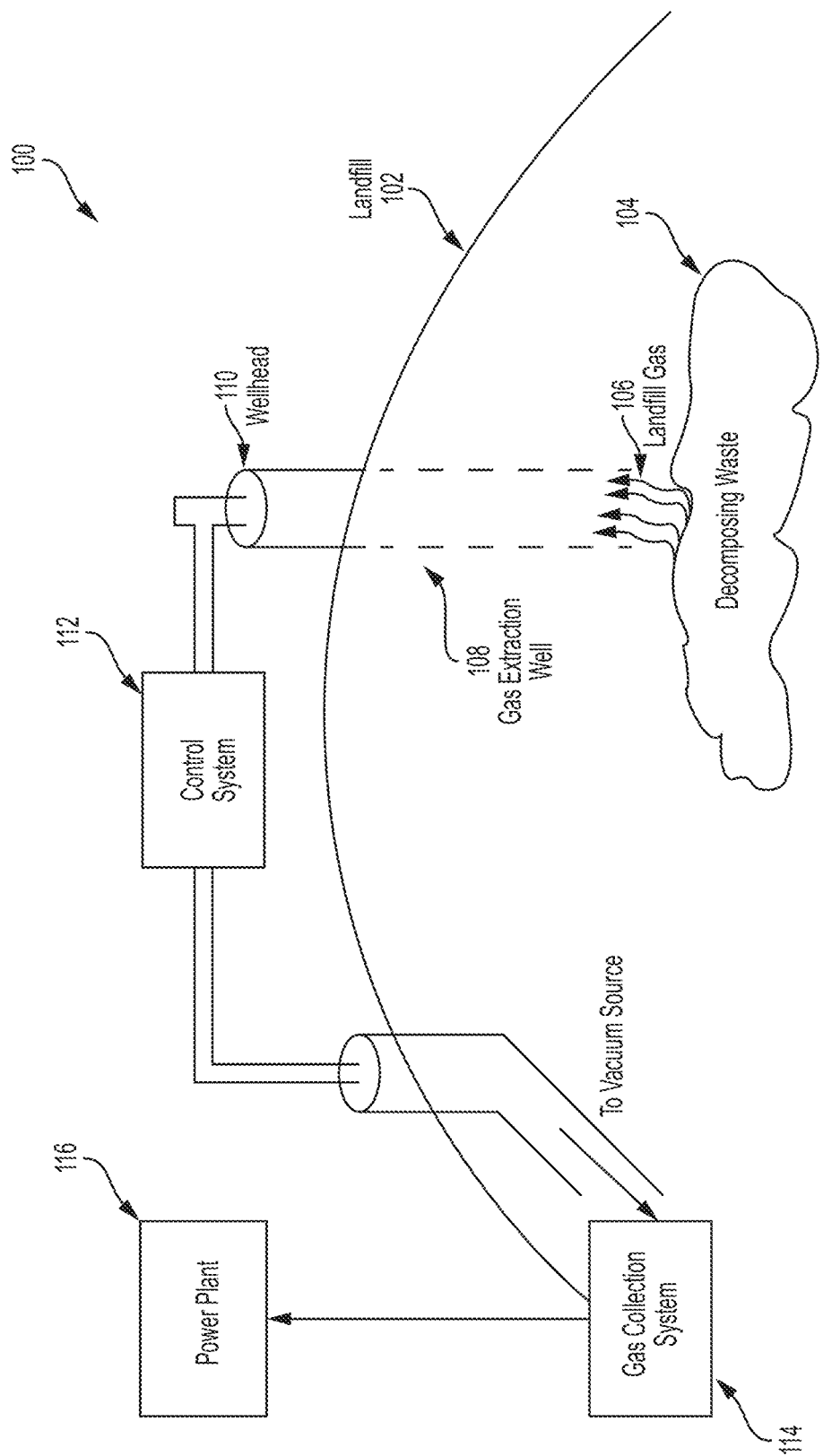
FIG. 1A shows an illustrative environment in which aspects of the technology described herein may be implemented.

Gas extraction systems control extraction of gas from a landfill to meet one or more objectives. For example, the objective(s) may include maximizing an energy content of gas extracted from the landfill (e.g., by maximizing an amount or concentration of methane in the gas, and/or by setting a flow rate to maximize the energy content), ensuring that extracted complies with regulations (e.g., government regulations), lowering an environmental impact of extracted gas, obtaining a specific composition of specific gases (e.g., methane, oxygen, carbon dioxide) in the extracted gas, and/or meeting an energy demand (e.g., of a power plant). Some gas extraction systems rely on sensor measurements to accurately and reliably control the extraction of landfill gas to meet the objective(s). For example, gas extraction systems may rely on measurements of temperature, gas composition, pressure, and/or other properties of the landfill gas to control the extraction of landfill gas.

The inventors have recognized that sensor measurements used by a gas extraction system may be inaccurate, which may lead to sub-optimal or poor performance of the gas extraction system. For example, landfill gas is often humid and contains water vapor which condenses into liquid when the gas cools. The condensation of the water vapor may lead to exposure of one or more sensors to liquid, which results in inaccurate and/or imprecise sensor measurements. The exposure of the sensor(s) to liquid may result in damage of the sensor(s) requiring costly repairs and/or replacement.

Accordingly, the inventors have developed an improved control system that not only obtains more accurate sensor measurements, but also extends the lifetime of the sensors used by the control system. Some embodiments provide for a control system that heats landfill gas and obtains sensor measurements of landfill gas that is kept at a threshold temperature above the temperature at which the landfill gas was initially extracted. For example, the control system heats the landfill gas at a temperature that is above the dew point of the landfill gas. By doing so, the control system reduces condensation of water vapor, which leads to more accurate sensor measurements and extends the lifetime of the sensor(s).

Some embodiments provide for a control system that maintains the landfill gas at a temperature and obtains sensors measurements of the landfill gas at the temperature. For example, the extracted landfill gas may already be at or above the dew point of the landfill gas. By maintaining the landfill gas at least at the extracted temperature, the control system reduces condensation of water vapor, which leads to more accurate sensor measurements and extends the lifetime of the sensor(s).

Some embodiments provide for a control system that removes water vapor from gas and obtains sensor measurements of landfill gas that is dryer than landfill gas that was initially extracted. By reducing the amount of water vapor in the landfill gas, the control system reduces condensation of water vapor, which also leads to more accurate sensor measurements and extends the lifetime of the sensor(s).

Some embodiments described herein address all of the above-described issues that the inventors have recognized with conventional landfill gas extraction techniques. However, it should be appreciated that not every embodiment described herein addresses every one of these issues. It should also be appreciated that embodiments of the technology described herein may be used for purposes other than addressing the above-discussed issues of conventional landfill gas extraction techniques.

Accordingly, the inventors have developed an improved control system for automatically controlling extraction of landfill gas that measures landfill gas characteristic(s) more accurately than conventional systems for landfill gas extraction. In some embodiments, the control system developed by the inventors: (1) heats landfill gas to a temperature greater than the temperature of the landfill gas when it is extracted (e.g., at least a threshold amount of degrees Celsius greater than the temperature of the extracted landfill gas); (2) measures one or more characteristics of the heated landfill gas; and (3) controls landfill gas extraction using the measured characteristic(s). Measuring landfill gas characteristic(s) at such a temperature avoids the harmful effects of condensation and results in improved sensor accuracy and extended hardware lifetimes. Increased sensor accuracy, in turn, leads to more accurate control of the gas extraction process. In some embodiments, this may result in extracting a greater amount of energy from the landfill gas.

In some embodiments, the control system maintains a temperature of the landfill gas at a temperature. For example, the control system maintains the landfill gas at a temperature at which the landfill gas was extracted. In another example, the control system maintains the temperature of the landfill gas at a temperature greater than the temperature at which the landfill gas was extracted. Maintaining the temperature of the landfill gas avoids condensation and results in improved sensor accuracy.

In some embodiments, the control system: (1) condenses landfill gas to cause water vapor in the landfill gas to form into liquid water; (2) removes the liquid water; (3) measures one or more characteristics (e.g. relative humidity, gas composition) of the landfill gas after the condensing; and (4) controls landfill gas extraction using the measured characteristic(s). Measuring the landfill gas characteristic(s) after removing water vapor from the landfill gas improves sensor accuracy and extends hardware lifetimes. Increased sensor accuracy, in turn, leads to more accurate control of the gas extraction process. In some embodiments, this may result in extracting a greater amount of energy from the landfill gas.

In some embodiments, the control system may be configured to both condense the landfill gas and heat the landfill gas prior to measuring the landfill gas characteristic(s). In some embodiments, the control system may be configured to heat the landfill gas without condensing the landfill gas. In some embodiments, the control system may be configured to condense the landfill gas without heating the landfill gas.

In some embodiments, the control system controls extraction of landfill gas from a landfill via a gas extraction system, with the landfill gas having a first temperature (e.g., 45 degrees Celsius) when extracted. The gas extraction system may be configured to include a vacuum source for creating a pressure differential between gas in the landfill and the vacuum source. As a result of the pressure differential, gas may flow from a well in the landfill through the gas extraction system towards the vacuum source through well piping. The control system may comprise a gas composition chamber coupled to the well piping. The gas composition chamber may include one or more sensors to measure one or more characteristics of a landfill gas sample collected in the gas composition chamber. The control system may include a temperature control mechanism to heat the landfill gas sample in the gas composition chamber to a second temperature that is a threshold amount (e.g., one, 10, or 25 degrees Celsius) greater than the first temperature. The control system may comprise a controller that controls a sensor to measure the characteristic(s) of the landfill gas sample in the gas composition chamber when the landfill gas sample in the gas composition chamber is at least the threshold amount greater than the first temperature.

In some embodiments, the second temperature (i.e., temperature at which measurements are taken) may be at least one, 10, or 25 degrees Celsius greater than the first temperature (i.e., the temperature of the gas when extracted). In some embodiments, the second temperature may be at least 5, at least 10, at least 15, at least 20, at least 25, at least 30, at least 35, at least 40, at least 45, or at least 50 degrees Celsius greater than the first temperature. In some embodiments, the second temperature may be greater than the first temperature by any temperature in the range of 1-10 degrees Celsius. In some embodiments, the second temperature may be greater than the first temperature by any temperature in the range of 5-25 degrees Celsius. In some embodiments, the second temperature may be greater than the first temperature by any temperature in the range of 5-50 degrees Celsius. In some embodiments, the second temperature may be greater than the first temperature by any temperature in the range of 1-50 degrees Celsius. In some embodiments, the second temperature may be greater than the first temperature by at least an amount that ensures that the water vapor in extracted landfill gas will not condense. Although reference is made to specific threshold temperature values, some embodiments are not limited to any one or set of threshold temperature values mentioned herein.

In some embodiments, the control system may be configured to maintain the temperature of the landfill gas sample in the gas composition chamber at a constant temperature greater than or equal to the second temperature. In some embodiments, the controller may include a proportional integral derivative (PID) controller which maintains the landfill gas sample at the constant temperature. In some embodiments, the control system may be configured to maintain the temperature at least at 30, 35, 40, 45, 50, 55, 60, 65, or 70 degrees Celsius. In some embodiments, the controls system may further be configured to prevent the temperature of the landfill gas sample from exceeding 30, 35, 40, 45, 50, 55, 60, 65, or 70 degrees Celsius. In some embodiments, the control system may be configured to maintain the temperature at least at a temperature between 50-100 degrees Celsius. In some embodiments, the control system may be configured to prevent the temperature of the landfill gas sample from exceeding a temperature between 50-100 degrees Celsius. Although reference is made to specific constant temperature values, some embodiments are not limited to any one or set of constant temperature values mentioned herein.

In some embodiments, the temperature control mechanism may include a heating element, for example, a resistive surface to generate heat for heating the landfill gas sample in the gas composition chamber. For example, the control system may be configured to generate an electrical current that flows through the resistive surface to generate heat for heating the landfill gas sample. In some embodiments, the gas composition chamber may have a surface made of a conductive material that conducts heat generated by the heating element. For example, the gas composition chamber may have a surface made of aluminum or stainless steel. The conductive surface may allow heat to flow to the landfill gas sample in the gas composition chamber. In some embodiments, the heating element may be placed in the gas composition chamber. In some embodiments, the heating element may be placed on the outside of the gas composition chamber. In some embodiments, the gas composition chamber may comprise a polymer. In some embodiments, the gas composition chamber may comprise a thermoplastic.

In some embodiments, the gas composition chamber may include an insulative material to insulate heat in the gas composition chamber. For example, the gas composition chamber may have an insulation layer (e.g., an aerogel, foam, polymer, or plastic insulation) placed around the gas composition chamber to prevent heat from flowing out of the gas composition chamber.

In some embodiments, the gas composition chamber may comprise a first temperature sensor which measures the temperature of the landfill gas in the gas composition chamber. In some embodiments, the control system may comprise a second temperature sensor that measures the first temperature of the extracted landfill gas (i.e., the temperature of the landfill gas when extracted).

In some embodiments, the control system may be configured to control extraction of landfill gas from the landfill through a gas extraction system. When the landfill gas is first extracted (e.g., before entering a gas composition chamber), the landfill gas has a first temperature (e.g., 45 degrees Celsius). In some embodiments, the control system controls the extraction of the landfill gas by (1) obtaining a sample of landfill gas in a gas composition chamber; (2) heating the landfill gas sample in the gas composition chamber to a second temperature at least a threshold amount (e.g., 1, 10, or 25 degrees Celsius) greater than the first temperature; and (3) controlling at least one sensor to measure one or more characteristics of the landfill gas sample in the gas composition chamber when a temperature of the landfill gas in the gas composition chamber is at least the threshold amount greater than the first temperature. In some embodiments, the gas extraction system may include a flow control mechanism (e.g., a valve), and the control system may be configured to control the flow control mechanism based on the measured characteristic of the landfill gas sample in the gas composition chamber. For example, the control system may be configured to adjust a position of a valve of the gas extraction system to adjust the flow rate of gas being extracted from the landfill.

In some embodiments, the control system may be configured to measure a concentration of methane in the landfill gas sample in the gas composition chamber. In some embodiments, the control system may be configured to determine an energy content of the landfill gas based on the measured concentration of methane. In some embodiments, the gas extraction system may comprise a flow control mechanism (e.g., a valve) and the control system may be configured to control the flow control mechanism (e.g., by adjusting a position of the valve) based on the determined energy content. The control system may be configured to control the flow control mechanism based on the energy content by determining whether the measured energy content is different from a target energy content, and when it is determined that the measured energy content is different from the target energy content, automatically controlling the at least one flow control mechanism to change energy content of the landfill gas being extracted from the landfill.

It should be appreciated that the systems and techniques introduced above and discussed in greater detail below may be implemented in any number of ways, as the techniques are not limited to any particular manner of implementation. Examples of details of implementation are provide herein solely for illustrative purposes. Furthermore, the techniques disclosed herein may be used individually or in any suitable combination, as aspects of the technology described herein are not limited to the use of any particular technique or combination of techniques.

FIG. 1A illustrates an example environment 100 in which aspects of the technology described herein may be implemented. The illustrative environment 100 includes a landfill 102 which holds decomposing waste 104. The decomposing waste 104 produces landfill gas (LFG) 106 which is extracted through a gas extraction well 108. The gas extraction well includes a wellhead 110 through which a control system 112 is coupled to the gas extraction well 108. The control system 112 may be configured to control extraction of gas via the gas extraction well 108. A gas collection system 114 collects the landfill gas 106 extracted through the gas extraction well 108. The gas collection system 114 supplies the extracted landfill gas to a power plant 116. Although in the example embodiment shown in FIG. 1A, a single wellhead 110 is shown, in some embodiments, the environment 100 may include multiple wellheads at multiple sites. In such embodiments, the landfill gas may be extracted from the multiple sites.

In some embodiments, the gas collection system 114 includes a vacuum source. The vacuum source generates a negative pressure differential between the gas collection system 114 and the landfill 102. The negative pressure differential causes the landfill gas 106 to flow from the landfill 102 to the gas collection system 114 through the gas extraction well 108. In some embodiments, the gas collection system 114 may comprise an additional location where extracted landfill gas is stored, and where the extracted landfill gas may be treated (e.g., by removing impurities) before being supplied to the power plant or to the pipeline infrastructure 116. The power plant 116 may be configured to convert the extracted landfill gas into electrical power. For example, the power plant 116 may be configured to burn the extracted landfill gas to turn a rotor of an electricity generator or a turbine.

It should be appreciated, that although FIG. 1A illustrates supplying of extracted landfill gas from the collection system 114 to a power plant 116, the extracted landfill gas may additionally or alternatively be supplied to one or more other locations, and/or used for other purposes. For example, the gas collection system 114 may be configured to supply gas to existing gas pipelines, boilers, greenhouses, heating units, and/or other locations, as aspects of the technology described herein are not limited with respect to where the extracted landfill gas is supplied.

In some embodiments, the control system 112 controls extraction of the landfill gas 106 through the gas extraction well 108. In some embodiments, the control system 112 may be configured to operate to control extraction of landfill gas to achieve a desired outcome or outcomes with respect to energy content of extracted landfill gas, composition of extracted landfill gas, flow rate of gas extraction, regulatory requirements, and/or other parameters. In some embodiments, the control system 112 may include multiple components that operate to achieve the outcome(s), as discussed in more detail herein.

Figure 1B:
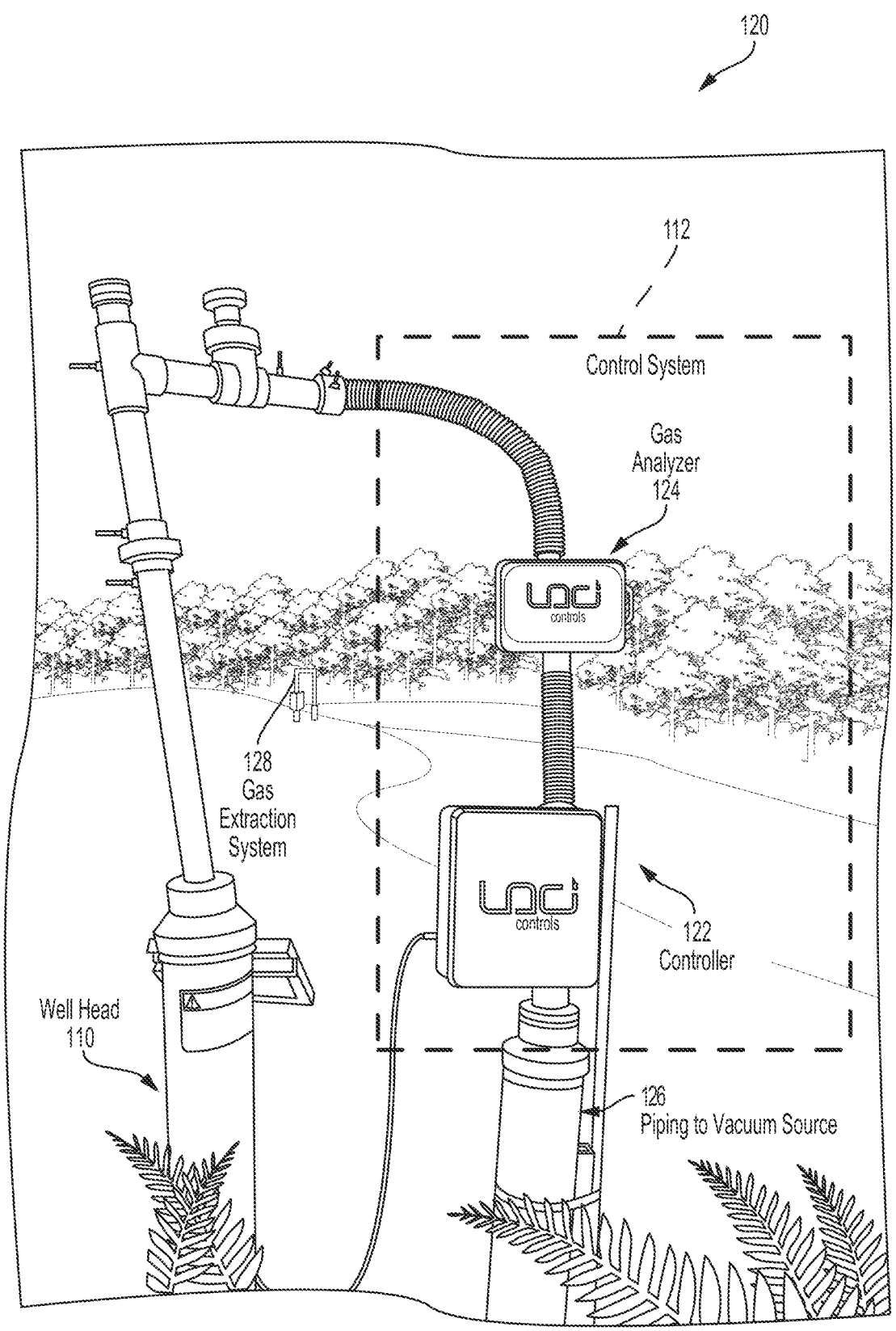
FIG. 1B shows an example control system for landfill gas extraction, in accordance with some embodiments of the technology described herein.

FIG. 1B illustrates an example implementation of the control system 112 for a landfill gas extraction system 120. The gas extraction well 108 may be coupled to the vacuum source through the piping 126 that leads to the vacuum source. Landfill gas may flow from the gas extraction well 108 towards the vacuum source via the piping 126. In some embodiments, the control system 112 is disposed within the piping 126 such that the control system 112 controls the flow of gas from the wellhead 110 to the vacuum source via the piping 126. The control system 112 includes a gas analyzer 124 which the control system 112 uses to determine one or more characteristics of the extracted landfill gas. The control system 112 includes a controller 122 that uses the determined characteristic(s) to control extraction of landfill gas. In some embodiments, the controller 122 may be configured to use the measured characteristic(s) to control a flow rate of landfill gas extraction. For example, the controller 122 may be configured to use the measured characteristic(s) to control a position of a valve that controls the flow rate of landfill gas being extracted.

In some embodiments, the gas analyzer 124 may be configured to collect and analyze extracted landfill gas. The gas analyzer 124 may be configured to include one or more sensors to measure the characteristic(s) of the extracted landfill gas. In some embodiments, the gas analyzer 124 may be configured to use the sensor(s) to measure composition, temperature, and/or other characteristic of the extracted landfill gas. In some embodiments, the gas analyzer may be configured to use the sensor(s) to measure the characteristic(s) of landfill gas when the gas is extracted (e.g., before being analyzed by the gas analyzer 124). The sensor(s) may comprise, for example, infrared sensors, catalytic beads, electrochemical sensors, photoionization detectors, zirconium oxide sensors, thermal conductive detectors, and/or any other suitable sensing technology for measuring the characteristic(s) of the landfill gas, as aspects of the technology described herein are not limited to using a particular type of sensor.

In some embodiments, the gas analyzer 124 may be configured to heat the landfill gas within gas composition chamber prior to measuring the characteristic(s) to obtain more accurate and/or consistent measurements of the characteristic(s). In some embodiments, the gas analyzer 124 may be configured to heat the extracted landfill gas prior to measuring the characteristic(s) of the landfill gas. In some embodiments, the gas analyzer 124 may be configured to heat the extracted landfill gas to a temperature that is a threshold temperature (e.g., 1 degree Celsius, 10 degrees Celsius, 25 degrees Celsius) greater than a temperature of the gas in the landfill and/or a temperature of the gas when it is extracted. The gas analyzer 124 may be configured to obtain measurements of the characteristic(s) of the extracted landfill gas at the higher temperature. By heating the extracted landfill gas in this manner prior to measuring the characteristic(s), the obtained measurements may be more accurate and precise. Further, the warmer landfill gas may reduce deterioration of hardware components in the gas analyzer 124 by preventing condensation of water vapor on the hardware components.

In some embodiments, the gas analyzer 124 may be configured to additionally or alternatively treat the gas sample in other ways. For example, the gas analyzer 124 may be configured to treat a gas sample by cooling the gas sample, and/or drying the gas sample. In another example, the gas analyzer 124 may be configured to filter the gas to remove particles, filter the gas to remove contaminants or other chemicals, pressurize the gas, de-pressurize the gas, or treating the gas in another manner. In some embodiments, the gas analyzer 124 may be configured to obtain measurements of the characteristic(s) of a landfill gas sample after treating the gas sample.

In some embodiments, the gas analyzer 124 may be configured to determine one or more characteristics of the environment (e.g., ambient temperature, atmospheric pressure, wind direction, wind speed, precipitation, humidity), and/or gas in the landfill (e.g., temperature, composition, humidity). The gas analyzer 124 may include one or more sensors to obtain measurements of the characteristic(s). The sensors can include, for example, temperature sensors, humidity sensors, pH sensors, pressure sensors and/or any other type of sensor(s) for sensing environmental characteristics.

In some embodiments, the controller 122 may be configured to control one or more parameters of landfill gas extraction. In some embodiments, the controller 122 may be configured to control a flow rate of landfill gas being extracted from the landfill 102. In some embodiments, the control system 112 may include a flow control mechanism to control a flow rate of landfill gas extraction. For example, the control system 112 may include one or more valves and a valve actuator for changing the position of the valve(s) to control the flow rate. The controller 122 may be configured to determine and apply settings to the valve(s) to control the flow rate of landfill gas extraction (e.g., operate the valve actuator to change the position of the valve to a determined position). In some embodiments, the control mechanism is placed between the gas extraction well 108 and the gas collection system 114 such that gas being extracted through the gas extraction well 108 flows through the control mechanism on its way to the gas collection system 114.

In some embodiments, the controller 122 may be coupled to the gas analyzer 124. The controller 122 may be configured to use measurements obtained by the gas analyzer 124 to determine the control parameter(s). In some embodiments, the controller 122 may be configured to regulate the landfill gas flow rate based on the measurements obtained by the gas analyzer 124. To adjust the flow rate, in some embodiments, the controller 122 may be configured to adjust a valve position to modify the flow rate. The controller 122 may be configured to control a valve actuator (e.g., a valve drive buffer) to move the position of the valve in order to obtain a position. In some embodiments, the controller 122 may be configured to determine a target flow rate based on the measurements of the characteristic(s) obtained by the gas analyzer 124. The controller 122 may be configured to adjust the control mechanism (e.g., valve position) such that the flow rate is the target flow rate.

In some embodiments, the control system 112 may be configured to determine a measure of energy content of landfill gas being extracted from the landfill 102. The gas analyzer 124 may be configured to obtain a measurement of concentration of methane in extracted landfill gas. The controller 122 may be configured to determine a flow rate of the gas being extracted from the landfill. The control system 112 may be configured to determine an energy content of the landfill gas being extracted from the landfill 102 based on the concentration of methane and the flow rate. The controller may be configured to determine a target energy content of landfill gas being extracted from the landfill 102 and control a flow control mechanism to set the flow rate such that the energy content of the landfill gas being extracted reaches the target energy content.

Example systems and techniques for controlling extraction of landfill gas are described in U.S. Patent Application Publication No. 2017/0216893, entitled "DEVICES AND TECHNIQUES RELATING TO LANDFILL GAS EXTRACTION" filed on Mar. 13, 2017, incorporated herein by reference. Some embodiments may include one or more features of embodiments described in the referenced application.

In some embodiments, multiple wells or gas extraction systems may be located at a landfill to extract gas from the landfill. For example, FIG. 1B illustrates another well and gas extraction system 128 located at the landfill. In some embodiments, multiple gas extraction systems at the landfill may include the control system 112 for controlling extraction of landfill gas from the landfill. For example, gas extraction system may include the control system 112 to control extraction of landfill gas via the gas extraction system 128.

Although the gas analyzer 124 and the controller 122 are shown as separate components in FIG. 1A, in some embodiments, the gas analyzer 124 and controller 122 may be portions of a single unit. Some embodiments are not limited to any particular arrangement or combination of the gas analyzer 124 and the controller 122. Furthermore, functionality described for each of the gas analyzer 124 and the controller 122 may be interchanged between the two components, as some embodiments of the technology described herein are not limited in this respect.

Figure 1C:
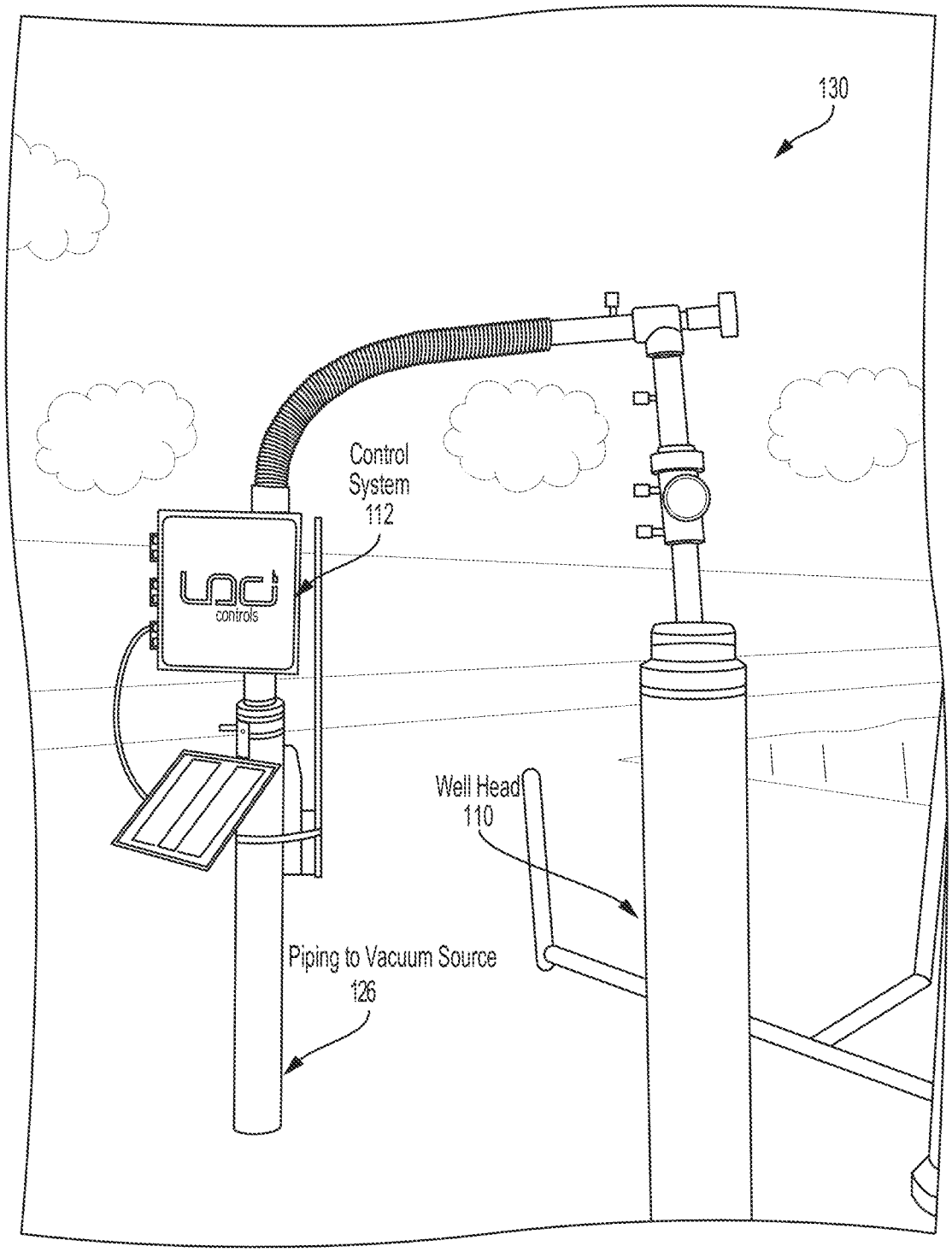
FIG. 1C shows another example control system for landfill gas extraction, in accordance with some embodiments of the technology described herein.

FIG. 1C illustrates an example implementation of the control system 112 for a landfill gas extraction system 130. In some embodiments, the gas analyzer and the controller described with reference to FIG. 1B are portions of the control system 112 shown in FIG. 1C. The gas extraction well 108 may be coupled to the vacuum source through the piping 126 that leads to the vacuum source. Landfill gas may flow from the gas extraction well 108 towards the vacuum source via the piping 126. In some embodiments, the control system 112 is disposed within the piping 126 such that the control system 112 controls the flow of gas from the wellhead 110 to the vacuum source via the piping 126. In some embodiments, the control system 112 may be configured to operate as described above with reference to FIG. 1B. For example, the control system 112 may be configured to use a gas analyzer and controller in the control system 112 to obtain measurements of one or more characteristics of the landfill gas being extracted via the gas extraction system and control extraction of the gas based on the measurements of the characteristic(s).

Figure 2:
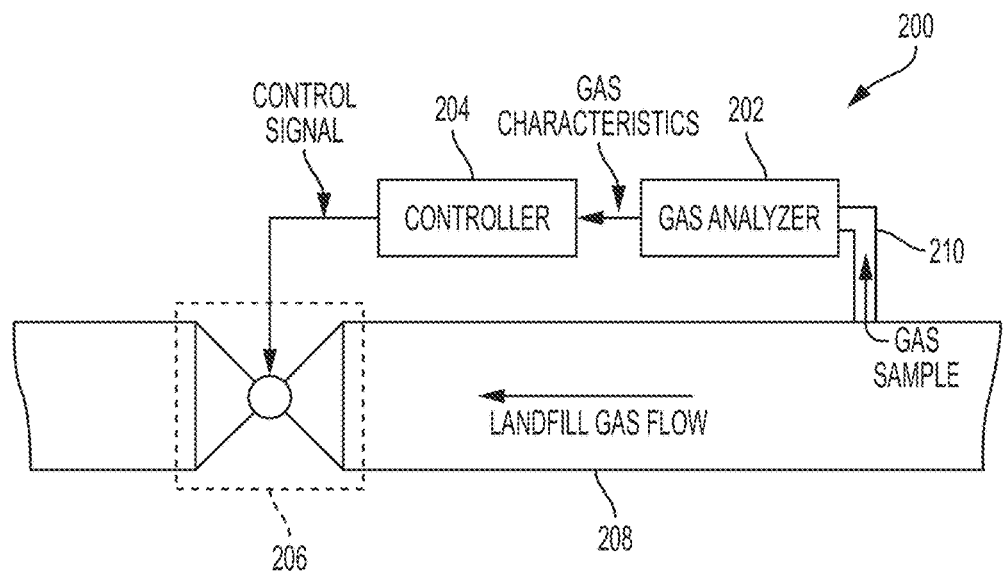
FIG. 2 is a block diagram illustrating components of an example landfill gas extraction control system, in accordance with some embodiments of the technology described herein.

FIG. 2 illustrates a block diagram of components of an example control system 200 for controlling extraction of gas via a gas extraction system, according to some embodiments of the technology described herein. In some embodiments, control system 200 may be a portion or all of control system 112 discussed above with respect to FIG. 1. For example, in some embodiments, the control system 200 may be configured to control flow of landfill gas from the landfill 102 through gas extraction well 108.

In some embodiments, the control system 200 includes a gas analyzer 202 for measuring one or more characteristic of landfill gas being extracted from the landfill. Measurements of the characteristic(s) of the landfill gas being extracted from the landfill may be used by a controller 204 to control a control mechanism 206. In some embodiments, the control mechanism 206 may be a flow control mechanism to control flow of landfill gas from the landfill to a gas collection system (e.g., gas collection system 114). For example, the flow control mechanism may include one or more valves that control flow rate of gas being extracted by the gas extraction system.

In some embodiments, the gas analyzer 202 may be configured to determine one or more characteristics of landfill gas and/or a surrounding environment of the landfill.

For example, the gas analyzer 202 may be configured to determine the characteristic(s) of extracted landfill gas, gas in the landfill, landfill gas in different portions of the gas extraction system, and/or landfill gas in a gas collection system. In some embodiments, the gas analyzer 202 includes one or more sensors to obtain measurements of the characteristic(s). In some embodiments, the gas analyzer 202 may be configured to obtain a sample of landfill gas from the gas extraction system 208 via an input port 210. The gas analyzer 202 may be configured to obtain measurements of the characteristic(s) of the collected gas sample. In some embodiments, the gas analyzer 202 may be configured to report the measurements of the characteristic(s) to the controller 204 for use in controlling the flow control mechanism 206.

In some embodiments, the gas analyzer 202 may be configured to obtain measurements for one or more characteristics of a collected gas sample or of landfill gas in the landfill. For example, the gas analyzer 202 may be configured to determine a temperature, pressure, flow rate, humidity, density, gas composition (e.g., concentration of methane, oxygen, carbon dioxide, carbon monoxide, hydrogen sulfide, nitrogen, and/or other gas) and/or any other suitable characteristic(s) of the collected gas sample. In some embodiments, the gas analyzer 202 may be configured to determine one or more characteristics of the landfill gas based on measurements obtained for a number of gas samples. For example, the gas analyzer 202 may be configured to determine an energy content of gas, or a concentration of methane in gas samples for a certain time period and/or across a number of collected gas samples. In some embodiments, the gas analyzer 202 may be configured to determine the characteristic(s) at a regular frequency. For example, the gas analyzer 202 may be configured to determine the characteristic(s) every second, every minute, every hour, every 12 hours, every 24 hours, every week, or at another frequency.

In some embodiments, the gas analyzer 202 may be configured to determine a gas composition of landfill gas being extracted from the landfill. In some embodiments, the gas analyzer 202 may be configured to determine a concentration of methane in a collected sample of gas. For example, the gas analyzer 202 may include one or more sensors configured to measure the concentration of methane in the sample of gas. The gas analyzer 202 may be configured to determine, using the determined concentration of methane, energy content of landfill gas being extracted from the landfill. The gas analyzer 202 may be configured to output the determined energy content to the controller 204 which may be configured to use the energy content to control the flow control mechanism 206.

In some embodiments, the gas analyzer 202 may be configured to heat a gas sample to improve measurement accuracy, resolution, and/or preciseness. In some embodiments, the gas analyzer 202 may be configured to also heat the collected gas sample(s) to decrease sensor hardware degradation. In some embodiments, the gas analyzer 202 may be configured to also treat the gas sample in other ways. For example, the gas analyzer 202 may be configured to treat a gas sample by heating the gas sample, cooling the gas sample, and/or drying the gas sample. In another example, the gas analyzer 202 may be configured to filter the gas to remove particles, filter the gas to remove contaminants or other chemicals, pressurize the gas, de-pressurize the gas, or treating the gas in another manner. In some embodiments, the gas analyzer 202 may be configured to obtain measurements of the characteristic(s) of a landfill gas sample after treating the gas sample.

In some embodiments, the control system 200 may include one or more sensors in addition to those shown in the gas analyzer 202. In some embodiments, the control system 200 may include one or more temperature and/or humidity sensors to measure ambient temperature and/or humidity outside of the landfill. The control system may include one or more sensors placed directly in gas extraction piping to obtain measurements of characteristics of the gas at different stages of the extraction system 208. In some embodiments, the control system 200 may include remote components (e.g., a computing device) for processing data to obtain the measurement(s) of the gas characteristic(s).

In some embodiments, the controller 204 may be configured to determine one or more settings of one or more control parameters and/or apply the control parameter(s) to the flow control mechanism 206. In some embodiments, the controller 204 may be configured to use measurements of one or more gas characteristics (e.g., energy content of landfill gas, temperature of landfill gas) determined by the gas analyzer 204 to control the flow control mechanism 206. U.S. Patent Application Publication No. 2017/0216893, entitled "DEVICES AND TECHNIQUES RELATING TO LANDFILL GAS EXTRACTION" filed on Mar. 13, 2017, incorporated herein by reference, describes example control parameters that may be controlled by the controller 204. In some embodiments, the controller 204 may be configured to determine a flow rate at which landfill gas is to flow through the gas extraction system 208. The flow rate may comprise a target flow rate for extracting landfill gas. In some embodiments, the controller 204 may be configured to determine the target flow rate based on energy content of landfill gas being extracted from the landfill. If the energy content of the landfill gas being extracted is different from a target energy content, the controller 204 may be configured to adjust the flow rate to change the energy content of landfill gas being extracted from the landfill.

In some embodiments, the flow control mechanism 206 may include a valve. The valve may be, for example, a solenoid valve, latching solenoid valve, pinch valve, ball valve, butterfly valve, ceramic disc valve, check valve, choke valve, diaphragm valve, gat valve, globe valve, or any other type of valve. Embodiments are not limited to a particular type of valve. Further, a flow control mechanism is not limited to valves alone as embodiments may be adapted for other types of flow control mechanisms.

In some embodiments, the flow control mechanism 206 may include one or more actuation devices configured to physically operate the flow control mechanism 206. For example, in embodiments in which the flow control mechanism includes a valve, the actuation device(s) may be configured to operate to open the valve, close the valve, and/or adjust a position of the valve. For example, the actuation device(s) may comprise a hydraulic actuator that uses hydraulic pressure to move a position of the valve. In another example, the actuation device(s) may comprise an electric actuator that uses an electric motor to provide a torque to operate a valve. In yet another example, the actuation device(s) may comprise a pneumatic actuator that uses air pressure to act on a piston to move the valve. Some embodiments are not limited to any specific type of actuation device, as any actuation device suitable for a respective flow control mechanism 206 may be used.

In some embodiments, to change flow rate, the controller 204 may be configured to control a valve position of the flow control mechanism 206. In some embodiments, the controller 204 may be configured to determine the valve position based on a target flow rate of landfill gas flowing through the gas extraction system 208. For example, the target flow rate may correspond to a setting that may achieve a target energy content in landfill gas being extracted from the landfill. In some embodiments, the controller 206 may be configured to control one or more actuation devices to apply the parameter(s) to the flow control mechanism 206. For example, in a system in which the actuation device(s) comprises an electrical actuator, the controller 204 may be configured to output a current or voltage to change position(s) of one or more valves. In another example, the controller 206 may be configured to apply fluid pressure to move the position(s) of the valve(s) via one or more fluid actuation devices.

Although, in the example embodiment illustrated in FIG. 2, the controller 204 is shown to be co-located with the landfill gas extraction system, in some embodiments one or more components of the controller 204 may be remote from the physical gas extraction system 208. For example, the controller 204 may include a computing device configured to perform flow control calculations and communicate settings remotely to a device disposed in piping between a gas extraction well and a vacuum source. The device may be configured to control the flow control mechanism based on settings received from the computing device. The computer device may be configured to communicate settings via wireless communication or by wired communication. In another example, the computing device may be configured to remotely control one or more actuation devices to adjust positions of one or more valves of the flow control mechanism.

Figure 3:
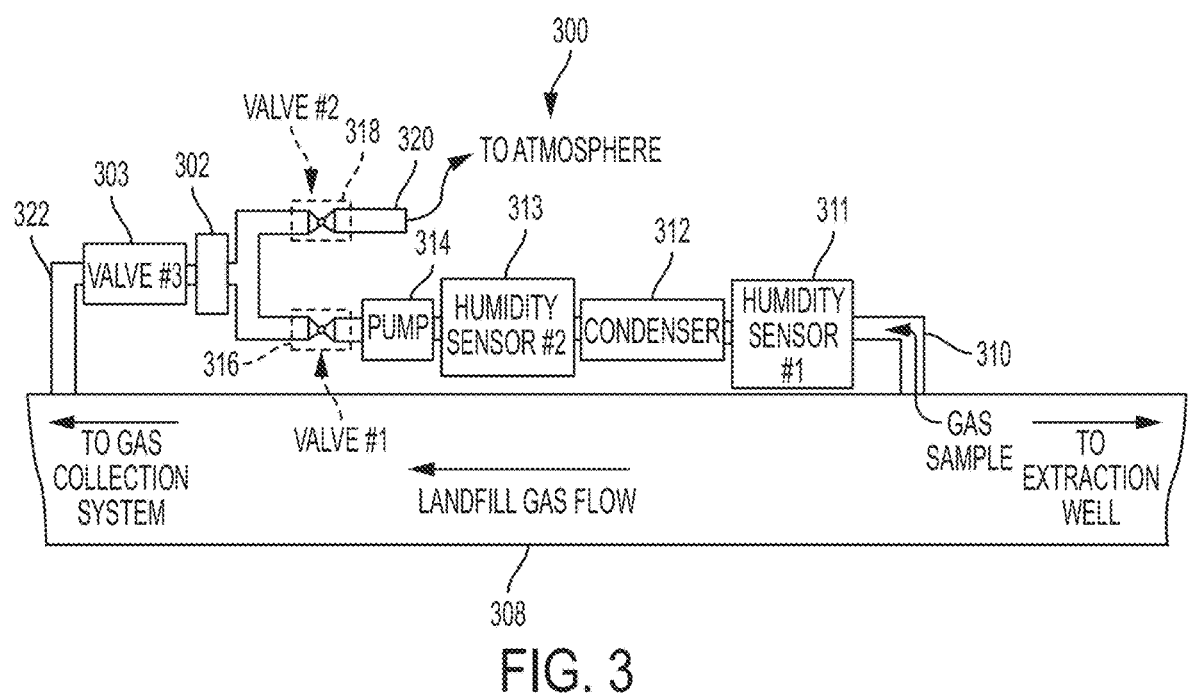
FIG. 3 is a block diagram illustrating components of an example gas analyzer, in accordance with some embodiments of the technology described herein.

FIG. 3 illustrates components of an example gas analyzer 300, in accordance with some embodiments of the technology described herein. For example, the gas analyzer 300 may be gas analyzer 202 discussed above in reference to FIG. 2 or gas analyzer 124 discussed above with respect to FIG. 1B. The gas analyzer 300 includes a gas composition chamber 302, an intake port 310, a pump 314, a first valve 316, and a second valve 318. The first valve 316 may be configured to open to allow the pump 314 to pump a gas sample received via intake port 310 into the gas composition chamber 302. In the gas composition chamber 302, the gas analyzer may be configured to measure one or more characteristics of the collected gas sample. After measuring the characteristic(s), the gas analyzer may be configured to open the second valve 318 to purge the collected landfill gas sample from the gas composition chamber 302.

In some embodiments, the gas analyzer 300 may be configured to receive a gas sample via intake port 310. In some embodiments, the intake port 310 may be coupled to a channel for landfill gas to flow to the gas analyzer from a main flow channel of the landfill gas extraction system 308. For example, the intake port 310 may be coupled to one or more pipes leading from a gas extraction well to the gas analyzer. A sample of landfill gas from landfill gas being extracted by the gas extraction system 308 may be routed to the gas analyzer by the pipe(s).

In some embodiments, the gas analyzer 300 is configured to obtain a sample of landfill gas to measure one or more characteristics of the sample of landfill gas by: (1) opening the first valve 316; (2) turning on the pump 314 to pump the gas sample through the opened first valve 316 into the gas composition chamber 302; (3) closing the first valve 316 once the gas sample has entered the gas composition chamber 302; (4) opening the third valve 303 to allow gas to exit the gas composition chamber 302 (5) turning off the pump 314. In some embodiments, the first valve 316 may be configured to remain open and the pump 314 turned on when the gas analyzer is measuring the characteristic(s) of the gas sample in the gas composition chamber 302.

In some embodiments, the gas analyzer 300 includes a condenser 312 that is configured to reduce humidity of a gas sample prior to the gas sample entering the gas composition chamber 302 via the first valve 316. For example, the condenser 312 may comprise a dehumidifying device that removes moisture from the gas sample. In some embodiments, the gas analyzer 300 includes a first humidity sensor 311 upstream of the condenser 312, and a second humidity sensor 313 downstream of the condenser. In some embodiments, the gas analyzer 300 may be configured to obtain measurements of the humidity of the landfill gas being extracted (e.g., of landfill gas before it enters the gas analyzer 300) using the first humidity sensor 311. The gas analyzer 300 may be configured to obtain measurements of the humidity of the landfill gas after undergoing condensation by the condenser 312 using the second humidity sensor 313.

In some embodiments, the condenser 312 may be configured to actively condense landfill gas being extracted prior to measuring one or more landfill gas characteristics (e.g., prior to entering the gas composition chamber 302). In some embodiments, the gas analyzer 300 may be configured to remove liquid water produced as a result of condensation. In some embodiments, the condenser 312 may include a mechanism by which to remove water produced as a result of condensation from the system. For example, the condenser 212 may include piping that directs the water away from the gas composition chamber 302. In some embodiments, the piping may direct the water out of the gas analyzer 300. For example, the piping may be coupled to an exit port through which water may be expelled from the gas analyzer 300.

In some embodiments, the condenser 312 may be configured to use the difference between the ambient temperature outside of the gas analyzer 300 and the temperature of the landfill gas extracted from the landfill (e.g., the landfill temperature) to condense the landfill gas. For example, the condenser 312 may be configured to expose the landfill gas to the atmosphere (e.g., by opening a valve to allow air from the atmosphere to reach the landfill gas) which may have a cooler temperature than the landfill temperature. As a result of exposure to the cooler temperature, water vapor may condense into liquid form. The condenser 312 may remove the water resulting from the condensation.

In some embodiments, the condenser 312 may be configured to actively condense the landfill gas. In some embodiments, the condenser 312 may use energy (e.g., in the form of electricity) to actively cool the landfill gas, and cause condensation of water vapor in the landfill gas. For example, the condenser 312 may use electricity to power a cooling device to cool a surface. When the landfill gas is exposed to the cooled surface, the temperature of the landfill gas may decrease, and water vapor in the landfill gas may condense to form liquid water. In some embodiments, the condenser 312 may add cooler air to the landfill gas to cause the temperature of the landfill gas to decrease and, in turn, cause water vapor in the landfill gas to condense to form liquid water. In some embodiments, the condenser 312 may use electricity generated by a power source such as a battery, solar panel, or other type of power source for generating electricity.

In some embodiments, the condenser 312 may be configured to use the first humidity sensor 311 and the second humidity sensor 313 to control condensation. For example, the condenser 312 may obtain measurements of the humidity of the landfill gas using the first humidity sensor 311, and measurements of the humidity of the landfill gas after undergoing condensation using the second humidity sensor 313. The condenser 312 may control one or more condensation parameters based on the difference between the measurements. For example, the condenser 312 may control a temperature of a cooling mechanism that causes condensation of a gas (e.g., control temperature of a cooling surface, or cooling air). In some embodiments, the condenser may comprise a controller (e.g., a PID controller) that controls condensation based on the difference in humidity. For example, the controller may control a temperature of a cooling mechanism based on the difference in humidity. In some embodiments, the condenser 312 may determine a target humidity to obtain for the landfill gas. In some embodiments, the target humidity may comprise a target difference in humidity between the landfill gas when it is first extracted and landfill gas after undergoing condensation by the condenser 312. In some embodiments, the target humidity may comprise a target humidity to obtain by condensing the landfill gas. The controller may control condensation to obtain the target humidity for the landfill gas. In some embodiments, the controller may be configured to maintain the humidity of the landfill gas at the target humidity and/or within a range of the target humidity.

In some embodiments, the gas analyzer 300 may include a single humidity sensor. The condenser 312 may be configured to obtain measurements of humidity of landfill gas after and/or while the condenser 312 has condensed the landfill gas using the single humidity sensor 313. The condenser 312 may then control condensation based on the obtained measurements. In some embodiments, the condenser 312 may determine whether the landfill gas has reached a target humidity based on the measurements obtained using the single humidity sensor. In some embodiments, the gas analyzer 300 may not include any humidity sensors. The condenser 312 may be configured to operate without using humidity values. For example, the condenser 312 may operate using measurements obtained from other sensors of one or more other characteristics (e.g., landfill gas temperature, ambient temperature, landfill gas pressure, atmospheric pressure). In some embodiments, the condenser 312 may be configured to operate without using any sensor measurements. For example, the condenser 312 may operate in a constant mode of operation without active automatic changing of settings by a controller.

In some embodiments, the gas analyzer 300 may not include a condenser 312, and/or the first and second humidity sensors 311, 313. For example, the gas analyzer may not condense landfill gas before allowing the landfill gas to enter the gas composition chamber 302. In some embodiments, the gas analyzer 300 may include one or more humidity sensors without a condenser 312. The gas analyzer 300 may be configured to use measurements obtained using humidity sensor(s) to correct measurements of one or more landfill gas characteristics for humidity. For example, the gas analyzer 300 may be configured to compensate measurements of methane, oxygen, carbon dioxide, and/or nitrogen concentration(s) in the landfill gas based on measurements of humidity.

In some embodiments, one or more humidity sensors in the gas analyzer may comprise a capacitive humidity sensor, a resistive humidity sensor, a thermal conductivity humidity sensor, and/or other sensing technology capable of measuring humidity. Some embodiments are not limited to any particular type of humidity sensor.

In some embodiments, the gas analyzer 300 may be configured to measure the characteristic(s) of the sample of landfill gas inside the gas composition chamber 302. In some embodiments, the gas analyzer 300 may include one or more sensors inside the gas composition chamber 302 that measure the characteristic(s) of the sample of gas. For example, the gas analyzer 300 may be configured to measure a temperature of the gas in the gas composition chamber 302. In another example, the gas analyzer 300 may be configured to measure a composition (e.g., a concentration of methane, oxygen, carbon dioxide, and/or nitrogen) of the gas sample in the gas composition chamber 302.

In some embodiments, after a sample of landfill gas has been measured by the gas analyzer 300, the gas analyzer 300 may be configured to purge the landfill gas sample from the gas composition chamber 302. In some embodiments, the gas analyzer may be configured to open the second valve 318 to purge the sample of landfill gas from the gas composition chamber. By opening the second valve 318, the landfill gas sample may exit from the gas analyzer 300 (e.g., into the atmosphere outside the landfill) via the second valve 318. In some embodiments, the gas analyzer may be configured to open the third valve 303 to purge the sample of landfill gas from the gas composition chamber 302. Opening the third valve 303 may be configured to force the landfill gas sample to flow to the gas collection system via the third valve 303. In some embodiments, the third valve 303 may be coupled to an exit port 322 through which landfill gas may flow from the gas composition chamber 302 to the gas collection system (e.g., via the main flow path of the gas extraction system 308). The gas collection system may be configured to be at a negative pressure relative to atmospheric pressure. As a result of the pressure differential, opening the second valve 318 may be configured to cause landfill gas in the gas composition chamber 302 to flow towards the gas collection system (e.g., out of the gas composition chamber via the third valve 303). When the landfill gas has been purged from the gas composition chamber 302, the gas analyzer may be configured to close the second valve 318 to prevent excess air (e.g., from the atmosphere) from leaking to the gas collection system.

In some embodiments, landfill gas in the gas composition chamber 302 may be purged by causing the landfill gas to flow to the gas collection system, or by causing the landfill gas to flow to the atmosphere via the second valve 318. For example, the gas analyzer 300 may be configured to purge the gas via valve #3 303 to the flow to the gas collection system. For example, a gas collection system may not always be at negative pressure relative to atmospheric pressure (e.g., if a vacuum source is down). In this case, the gas analyzer 300 may be configured to purge the landfill gas from the gas composition chamber via the second valve 318. In some embodiments, the pump 314 (or another pump not shown) may be used to force air through the second valve 318 and to the atmosphere to purge the gas composition chamber 302. For example, a third valve (not shown) may be placed between the intake port 310 and the pump 314. When the gas analyzer is purging air from the gas composition chamber 302 to atmosphere, the gas analyzer may be configured to close the third valve and turn on the pump 314 to force purge landfill gas from the gas composition chamber 302 to the atmosphere.

Although an example configuration of gas analyzer components is illustrated in FIG. 3, other configurations and/or components may be used to perform gas analysis in accordance with embodiments described herein. For example, the pump 314 may be placed after the first valve 316, or after the gas composition chamber 302, or the condenser 312 may be moved to a different point in the flow path. Similarly, the functionality provided by the first valve 316 and the pump 314 may be consolidated by use of a sealed pump design (e.g., a peristaltic pump). In some embodiments, the third valve 303 may be configured to control and/or prevent backflow into the gas composition chamber 302. Additionally, the gas analyzer may include additional modules to provide other pre-treatment of the gas in addition to or in alternative to the drying (e.g., particle filter, chemical removal device).

In some embodiments, the gas analyzer illustrated in FIG. 3 may be configured to use any type of valve for the first valve 316, the second valve 318, and/or any other valve in the gas analyzer. Example types of valves are described herein.

Figure 4A:
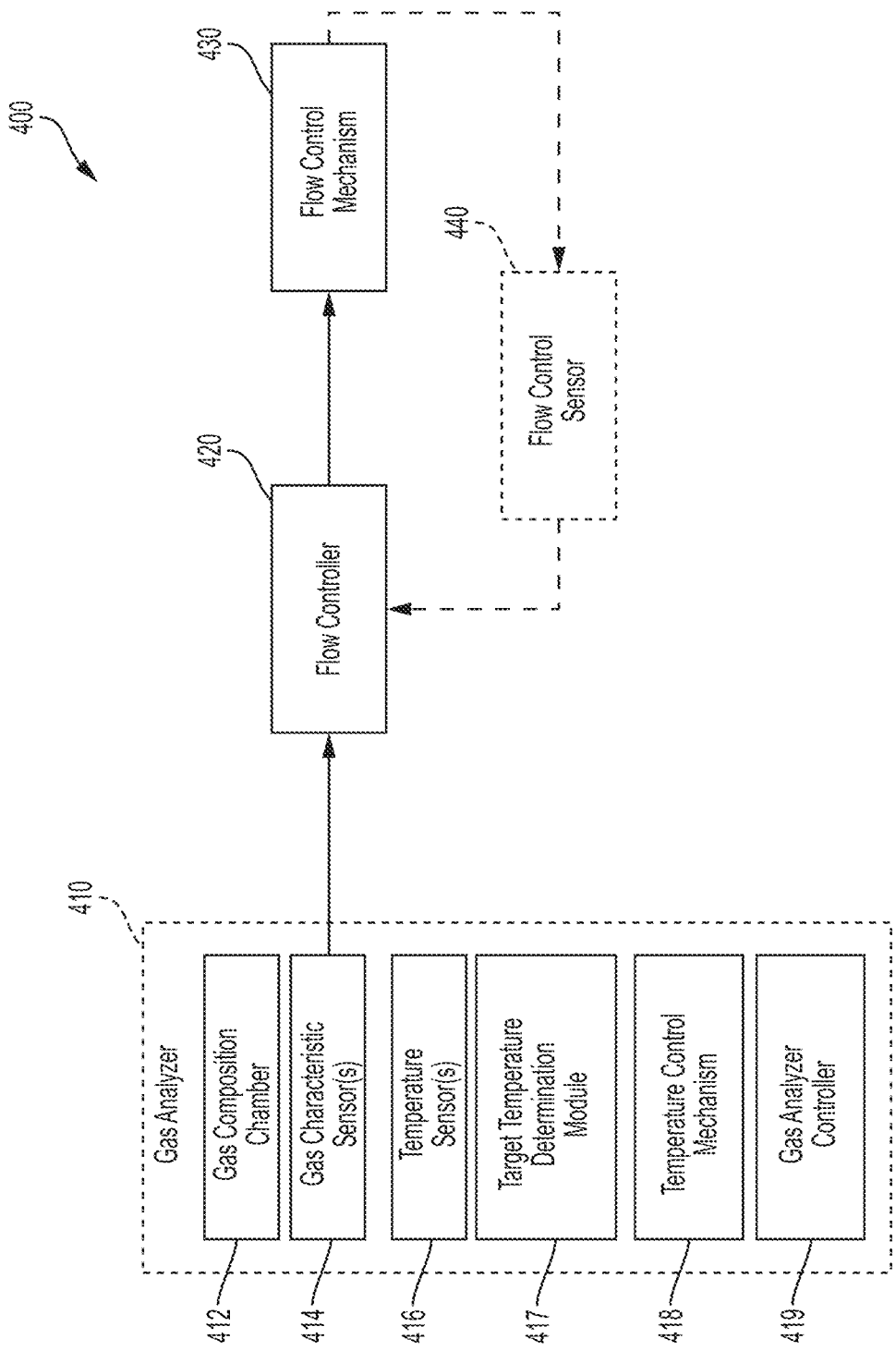
FIG. 4A is a block diagram illustrating components of an example gas analyzer and interaction of the gas analyzer with an example flow control mechanism, in accordance with some embodiments of the technology described herein.

FIG. 4A is a block diagram illustrating components of an example gas analyzer and interaction of the gas analyzer with an example flow control mechanism, in accordance with some embodiments of the technology described herein. As shown in FIG. 4A, the control system 400 includes a gas analyzer 410, a flow controller 420, a flow control mechanism 430, and a flow control sensor 440. The gas analyzer 410 provides measurements of one or more landfill gas characteristics to the flow controller 420. The flow controller 420 may be configured to use the measurements of the gas characteristic(s) to control the flow control mechanism 430. The flow control mechanism 430 may be configured to control a flow of landfill gas being extracted from the landfill via the flow control mechanism 430. In some embodiments, the flow control mechanism 430 may be configured to control a flow rate of landfill gas being extracted from the landfill.

In some embodiments, the gas analyzer 410 may be configured to obtain measurements one or more characteristics of landfill gas being extracted from the landfill. The gas analyzer 410 may be configured to transmit the measurements to the flow controller 420. In turn, the flow controller 420 may be configured to determine settings of control parameters to apply to the flow control mechanism 430 based on the measurements. In some embodiments, the gas analyzer 410 may be configured to obtain measurements of energy content of landfill gas being extracted from the landfill. The gas analyzer 410 may be configured to determine the measurements by measuring a composition of the landfill gas. In some embodiments, the gas analyzer 410 may be configured to determine a concentration of methane in the landfill gas. The gas analyzer 410 may be configured to determine energy content of the gas based on the concentration of methane in the landfill gas. In some embodiments, the gas analyzer 410 may be configured to use other information to determine the energy content of the landfill gas including ambient temperature, humidity, concentration of another gas, landfill gas temperature, pressure of landfill gas, and/or other parameters. Some embodiments are not limited to a particular set of parameters to use to determine the energy content.

In some embodiments, the flow controller 420 may be configured to determine settings to apply to the control flow mechanism 430 based on the measurements received from the gas analyzer 410. In some embodiments, the flow controller 420 may be configured to receive measurements of energy content of landfill gas being extracted from the landfill. The flow controller 420 may be configured to determine the settings based on the received measurements of energy content. In some embodiments, the flow controller 420 may be configured to control the flow control mechanism to obtain a target energy content of landfill gas being extracted from the landfill. The flow controller 420 may be configured to obtain the measurements of the current energy content of the landfill gas (e.g., from the gas analyzer 410). If the flow controller 420 determines that the current energy content is different than the target energy content, the flow controller 420 may be configured to determine to change settings of the flow control mechanism 430. For example, if the measured energy content is lower than the target energy content, the flow controller 420 may be configured to determine to change one or more valve settings (e.g., valve position(s)) to increase the flow rate of landfill gas extraction. In another example, the measured energy content may be higher than the target energy content. In this example, the flow controller 420 may be configured to determine to change the valve setting(s) to decrease the flow rate of landfill gas extraction. In yet another example, the measured energy content may be within a threshold of a target energy content. In this example, the flow controller 420 may be configured to determine to maintain the valve setting(s).

In some embodiments, the control system 400 may be configured to control based on one or more other gas characteristics. For example, the flow controller 420 may be configured to determine settings for the flow control mechanism 430 based on measurements of gas temperature and/or a target temperature, measurements of gas composition and/or a target gas composition, measurements of humidity of the landfill gas and/or target humidity of the landfill gas. In some embodiments, the flow controller 420 may be configured to determine one or more settings for the control flow mechanism 430 based on other parameters such as environmental factors (e.g., ambient temperature, ambient humidity). In some embodiments, the flow controller 420 may be configured to determine the setting(s) based on regulatory standards. For example, the flow controller 420 may be configured to adjust the settings(s) of the flow control mechanism 430 to ensure that one or more measurements are within regulatory limits for landfill gas being extracted from the landfill (e.g., limits on methane concentration, limits on oxygen concentration).

In some embodiments, the flow control mechanism 430 may comprise a valve. Examples of valves are provided herein. In some embodiments, other types of flow control mechanisms other than a valve may be used in place of a valve.

In some embodiments, the control system 400 may include a flow control sensor 440 coupled to the flow control mechanism 430 and the flow controller 420. As indicated by the dashed line connecting the flow control sensor 440 to the flow controller 420 and the flow control mechanism 430, the flow control sensor 440 may be optional. In some embodiments, the flow controller 420 may be configured to control the flow control mechanism 430 without feedback from the flow control mechanism. For example, the flow controller 420 may be configured to control the flow control mechanism 430 without the flow control sensor 440. In this example, the flow controller 420 may be configured to determine a setting for the flow control mechanism 430 (e.g., a valve position) based only the measurement(s) of the gas characteristic(s) received from the gas analyzer 410.

In some embodiments, the flow control sensor 440 feeds information back to the flow controller 420 about the flow control mechanism 430. For example, the flow control sensor 440 measures flow rate, an indication of a valve position, and/or other parameter about the flow control sensor 440. For example, the flow control sensor 440 may be configured to measure the flow rate based on a pressure differential across a venturi, orifice plate, or other constriction of the flow of gas. One or more measurements obtained by the flow control sensor 440 may be transmitted to the flow controller 420 which may be configured to use the measurement(s) to determine one or more settings of the flow control mechanism 430. For example, the flow controller 420 may be configured to determine a valve position at which to set a valve of the flow control mechanism 430 based on a flow rate measured by the flow control sensor 440.

In some embodiments, the flow controller 420 may comprise a proportional controller (P), a proportional integral controller (PI), and/or a proportional integral derivative controller (PID). The flow controller 420 may be configured to determine settings for the flow control mechanism 430. For example, the flow controller 420 may be configured to determine settings based on a target parameter (e.g., target energy content of gas, target flow rate, and/or target valve position). In some embodiments, the flow controller 420 may be configured to determine setting at a set frequency. For example, the flow controller 420 may be configured to determine settings for the control flow mechanism 430 every minute, hour, day, week, month, or other time period. Some embodiments are not limited to any specific period of frequency of setting determination.

Figure 4B:
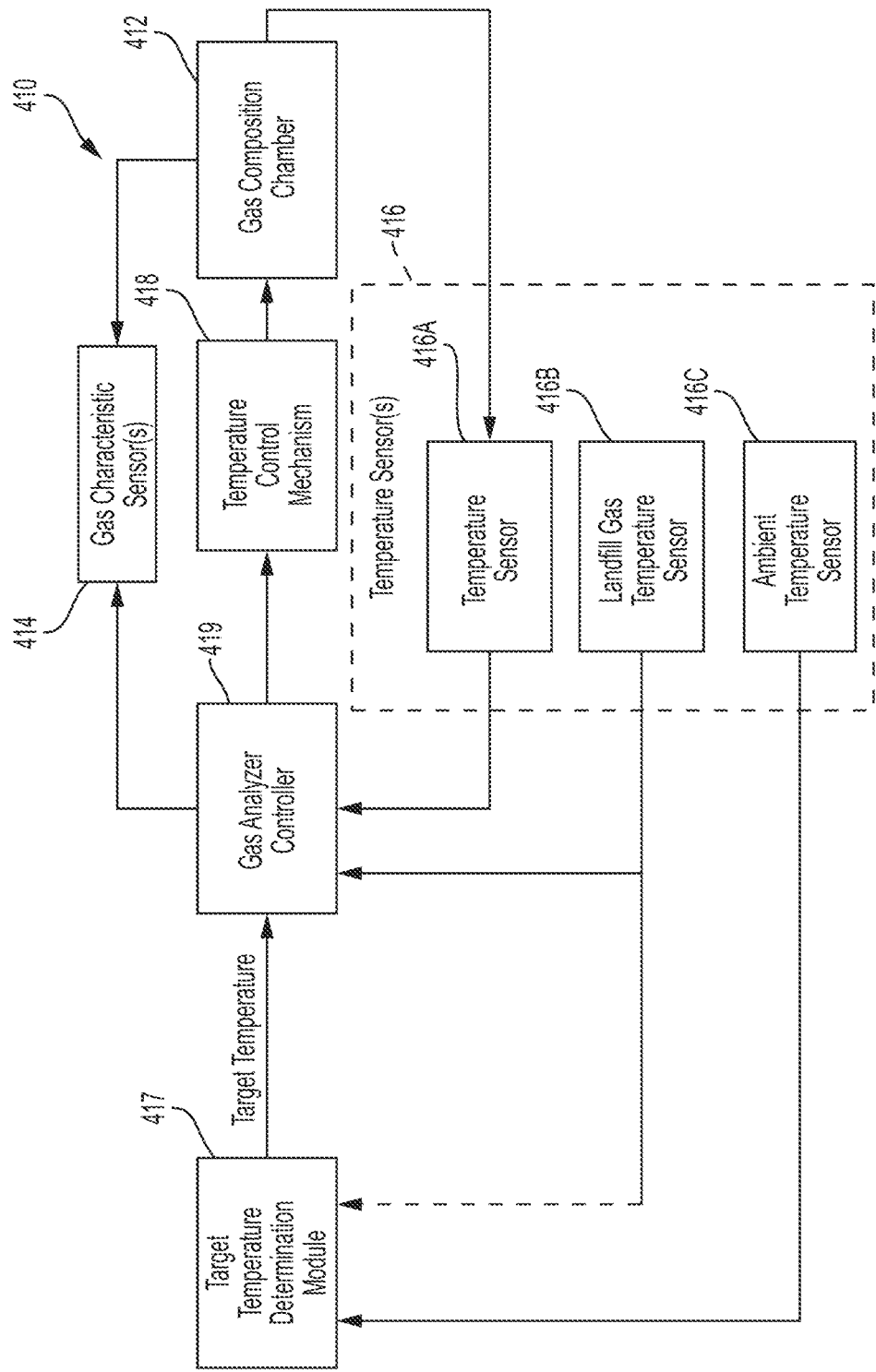
FIG. 4B is a block diagram illustrating interactions among components of the example gas analyzer shown in FIG. 4A, in accordance with some embodiments of the technology described herein.

In some embodiments, the gas analyzer 410 comprises a plurality of components for obtaining measurements of one or more gas characteristics. As shown in FIGS. 4A-B, the gas analyzer 410 comprises a gas composition chamber 412, one or more gas characteristic(s) sensors 414, one or more temperature sensors 416, a target temperature determination module 417, a temperature control mechanism 418, and a gas analyzer controller 419.

In some embodiments, the gas analyzer 410 may be configured to use the gas composition chamber 412 to obtain and hold a sample of landfill gas for measurement. As described above with reference to FIG. 3, the gas analyzer 410 may be configured to receive a landfill gas sample into the gas composition chamber 412, and analyze the gas sample in the chamber 412. In some embodiments, the gas composition chamber 412 may comprise a sealed chamber. The gas analyzer 410 may be configured to control entry and exit of gas into and out of the sealed chamber as described above with reference to FIG. 3. In some embodiments, the gas composition chamber 412 may comprise a pressurized chamber. In some embodiments, the gas composition chamber 412 may have a cylindrical shape, a spherical shape, a rectangular prism shape or other type of shape. Some embodiments are not limited to a specific shape of the gas composition chamber 412.

In some embodiments, the gas analyzer 410 includes one or more gas characteristic sensors 414 to measure one or more characteristics of landfill gas. In some embodiments, the gas characteristic sensor(s) may be configured to reside inside the gas composition chamber 412 to obtain measurements of the gas characteristic(s). For example, when the gas analyzer 410 obtains a sample of landfill gas in the gas composition chamber 412, the gas analyzer 410 may be configured to operate the gas characteristic sensor(s) 414 to obtain a measurements of the characteristic(s) of the sample of landfill gas in the gas composition chamber 412. In some embodiments, the gas characteristic sensor(s) may comprise one or more sensors for measuring a concentration of one or more gases (e.g., methane, oxygen, nitrogen, carbon dioxide) in the landfill gas sample. Examples of the sensor(s) are described herein. The gas analyzer 410 may be configured to operate the sensor(s) to obtain a measurement of the concentration of the one or more gases in the landfill gas sample. In some embodiments, the gas characteristic sensor(s) may include other types of sensors described herein.

In some embodiments, the gas analyzer 410 comprises a target temperature determination module 417, which determines a target temperature at which to measure the gas characteristic(s). In some embodiments, measurements obtained from gas characteristic sensor(s) 414 may be more accurate and/or precise at a certain temperature, in a temperature range, or above/below a threshold temperature. Further, obtaining a measurement at a constant known temperature may be configured to eliminate correction of measurements taken at various temperatures. In some embodiments, the gas characteristic sensor(s) 414 may be configured to measure more accurately and/or precisely when the temperature of the landfill gas in the gas composition chamber 412 is a threshold temperature above the temperature of the gas when it is extracted and/or when it is in the landfill. In some embodiments, the temperature of the landfill gas may have a first temperature (e.g., 45 degrees Celsius) prior to being collected in the gas composition chamber 412. The temperature determination module 417 may be configured to determine a target temperature at which to obtain measurements of the gas characteristic(s). In some embodiments, the target temperature may comprise a threshold temperature above first the temperature as described herein.

In some embodiments, the temperature determination module 417 may comprise a computer system configured to determine the target temperature at which to measure the gas characteristic(s). In some embodiments, the computer system may be co-located with the gas analyzer 410 and communicatively coupled to one or more components (e.g., the gas analyzer controller 419) of the gas analyzer 410. In some embodiments, the computer system may be located remotely and communicate the target temperature to one or more other components of the gas analyzer 410. For example, the temperature determination module 417 may be configured to transmit the target temperature to the gas analyzer controller 419. In some embodiments, the temperature determination module 417 may comprise a portion of the gas analyzer controller 419.

In some embodiments, the temperature determination module 417 may be configured to determine the target temperature based on one or more environmental conditions. For example, the temperature determination module 417 may be configured to determine the target temperature based on ambient temperature. In some embodiments, the temperature determination module 417 may be configured to determine the target temperature based on a period of the year (e.g., a season). For example, the temperature determination module 417 may be configured to determine a lower target temperature in a winter season than in a summer season because the temperature of gas in the landfill in the winter season may be lower than that of the gas in the landfill in the summer season. Accordingly, the system may be configured to heat the landfill gas to a lower target temperature in the winter season than in the summer season to heat a sample of landfill gas to a threshold temperature greater than the temperature of the gas in the landfill.

In some embodiments, the target temperature determination module 417 may include a humidity sensor to measure a humidity of the landfill gas. In some embodiments, the humidity sensor can be configured to measure a humidity of the landfill gas when the landfill gas is extracted from the landfill. The target temperature determination module 417 may be configured to measure the humidity of the landfill gas when it is extracted from the landfill. The temperature determination module 417 may be configured to determine a target temperature based on the humidity of the landfill gas. For example, the target temperature determination module 417 may be configured to estimate the dew point of the landfill gas based on the measured humidity. The target temperature determination module 417 may set the target temperature as a temperature that is greater than equal to the dew point of the landfill gas.

In some embodiments, the gas analyzer 410 may include one or more temperature sensors 416 configured to determine a temperature of landfill gas in the gas composition chamber 412 and/or to determine the temperature of the landfill gas in the landfill. In some embodiments, the sensor(s) 416 may comprise: (1) a first temperature sensor configured to measure the temperature of the landfill gas in the gas composition chamber 412; and (2) a second temperature sensor to measure the temperature of the landfill gas in the landfill (e.g., prior to entering the gas composition chamber 412). The first temperature sensor may be placed in the gas composition chamber 412 so that the first temperature sensor may be configured to measure a temperature of a landfill gas sample in the gas composition chamber to obtain a first temperature. The second temperature sensor may be placed outside of the gas composition chamber 412 and determine a temperature of gas when it is extracted and/or when the gas is in the landfill. For example, the second temperature sensor may be placed upstream of the gas composition chamber 412 such that the second temperature sensor may be configured to measure a temperature of the gas prior to being collected in the gas composition chamber 412.

As shown in FIG. 4A, the gas analyzer 410 includes a temperature control mechanism 418 that controls the temperature of landfill gas in the gas composition chamber 412. In some embodiments, temperature control mechanism 418 may include a heating element by which the temperature control mechanism 418 may be configured to heat landfill gas in the gas composition chamber 412. In some embodiments, the heating element may comprise a resistive surface. The temperature control mechanism 418 may be configured to generate an electric current that flows through the resistive surface causing the resistive surface to generate heat. The resistive surface may be placed in contact with a surface of the gas composition chamber 412 such that the gas composition chamber 412 may be configured to absorb heat generated by the heating element (e.g., the resistive surface). In some embodiments, the gas composition chamber 412 may comprise a conductive surface that conducts heat receives from the resistive surface. Landfill gas in the gas composition chamber 412 may be configured to absorb the heat, resulting in an increase in temperature of the landfill gas in the gas composition chamber 412. In some embodiments, the temperature control mechanism 418 may include a voltage or current generator connected to the resistive surface in a circuit. The voltage or current generator may be configured to generate a current in the resistive surface via the circuit.

Though embodiments described herein refer to a temperature control mechanism 418 comprising a resistive surface for heating landfill gas in the gas composition chamber 412, embodiments may be configured with other types of heating elements. The temperature control mechanism may comprise a radiator, heat pump, combustion heater, or other heating element for heating landfill gas in the gas composition chamber 412, as aspects of the technology described herein are not limited to a particular type of temperature control mechanism.

In some embodiments, the gas analyzer 410 includes a gas analyzer controller 419 that controls the temperature control mechanism 418 to heat landfill gas in the gas composition chamber 412. In some embodiments, the gas analyzer controller 419 receives a target temperature from the target temperature determination module 417. The gas analyzer controller 419 may be configured to control the temperature control mechanism to heat landfill gas in the gas composition chamber 412 based on the target temperature. In some embodiments, the gas analyzer controller 419 may include a PID controller for controlling the temperature control mechanism 418 to heat the landfill gas in the gas composition chamber. For example, the PID controller may be configured to control the temperature control mechanism 418 such that a collected sample of landfill gas may reach a target temperature. In another example, the PID controller may be configured to control the temperature control mechanism 418 to maintain the temperature of the collected sample of landfill gas at least at the target temperature. In some embodiments, the gas analyzer controller 419 may further prevent the temperature of the landfill gas from exceeding a temperature. In some embodiments, the gas analyzer controller 419 may prevent the landfill gas from exceeding a limit specified by regulations (e.g., government, environmental protection agency (EPA) regulations).

In some embodiments, the gas analyzer controller 419 may be configured to control the gas characteristic sensor(s) to obtain measurements of the gas characteristic(s). In some embodiments, the gas analyzer controller 419 may be configured to determine when to take a measurement. In some embodiments, the gas analyzer controller 419 may be configured to determine when to take a measurement based on temperature of the landfill gas in the gas composition chamber. For example, the gas analyzer controller 419 may be configured to trigger a measurement when the landfill gas in the gas composition chamber 412 has reached a target temperature (e.g., provided by target temperature determination module 417). In some embodiments, the gas analyzer controller 419 may be configured to determine when to take a measurement based on the temperature of the landfill gas in the gas composition chamber relative to the temperature of the landfill gas in the landfill. For example, the gas analyzer controller 419 may be configured to trigger a measurement when the landfill gas in the gas composition chamber 412 is at least a threshold temperature above the landfill gas in the landfill. For example, the threshold may be provided by the target temperature determination module 417.

FIG. 4B is a block diagram illustrating interactions among components of the example gas analyzer 410 shown in FIG. 4A, in accordance with some embodiments of the technology described herein. In some embodiments, the target temperature determination module 417 determines a target temperature for obtaining measurements of one or more gas characteristics. The target temperature determination module 417 may be configured to obtain temperature measurements from one or more temperature sensors 416 of the gas analyzer 410. In some embodiments, the target temperature determination module 417 may be configured to obtain a temperature of landfill gas in the landfill (e.g., a landfill temperature) from a landfill temperature sensor 416B. The target temperature determination module 417 may be configured to use the measurement of the landfill temperature to determine a threshold temperature above the landfill temperature at which to obtain measurement(s) of the gas characteristic(s). In some embodiments, the target temperature output by the module 417 may comprise a temperature to which the landfill gas in the gas composition chamber 412 is to be heated. In some embodiments, the target temperature outputted by the module 417 may comprise a threshold temperature value indicating how much higher than the landfill temperature the landfill gas in the gas composition chamber 412 is to be heated to.

In some embodiments, the target temperature determination module 417 may be configured to obtain (1) an ambient temperature of the environment outside the landfill from an ambient temperature sensor 416C, and (2) a temperature of the landfill gas from a landfill gas temperature 416B. The target temperature determination module 417 may be configured to use the ambient temperature and the landfill gas temperature to determine the target temperature. The target temperature determination module 417 can be configured to determine a target temperature that is a threshold temperature (e.g., 1, 10, or 25 degrees Celsius) above the temperature of the landfill gas. In some embodiments, the target temperature determination module 417 may be configured to obtain an ambient temperature of the environment outside the landfill from an ambient temperature sensor 416C without obtaining the temperature of the landfill gas as indicated by the dashed arrow. In some embodiments, the target temperature determination module 417 may be configured to use the ambient temperature measurement to determine the target temperature. In some embodiments, the temperature determination module 417 may be configured to adjust the threshold temperature above the landfill temperature that the landfill gas in the gas composition chamber 412 is to be heated to for taking measurements (e.g., to ensure accurate and/or precise characteristic(s) measurement(s)). For example, the temperature determination module 417 may be configured to determine that the temperature at which landfill gas characteristic(s) measurements are taken in the gas composition chamber 412 is at least 10 degrees Celsius higher than the landfill gas temperature to ensure accurate measurement(s) of the characteristic(s). In another example, the temperature determination module 417 may be configured to determine that, to ensure accurate measurement(s) of the characteristic(s), the landfill gas is to be at least 25 degrees Celsius higher than the landfill temperature to ensure accurate measurement(s) of the characteristic(s).

In some embodiments, the target temperature determination module 417 may be configured to output a target temperature to the gas analyzer controller 419. The gas analyzer controller 419 may be configured to control the temperature control mechanism 418 to heat landfill gas in the gas composition chamber 412 based on the target temperature. The gas analyzer controller 419 may be configured to receive a temperature measurement of landfill gas in the gas composition chamber 412 from temperature sensor 416A. In some embodiments, the temperature sensor 416A may be in the gas composition chamber 412 such that the temperature sensor 416A may be configured to measure temperature of a landfill gas sample in the gas composition chamber 412.

In some embodiments, the gas analyzer controller 419 may be configured to control the temperature control mechanism 418 to heat the landfill gas in the gas composition chamber 412 to at least the target temperature (e.g., received from the target temperature determination module 417). In another embodiment, the gas analyzer controller 419 may be configured to control the temperature control mechanism 418 to heat the landfill gas in the gas composition chamber to at least a threshold temperature higher than the landfill temperature. The gas analyzer controller 419 may be configured to receive temperature measurements from the landfill temperature sensor 416B and determine whether the temperature of the landfill gas in the gas composition chamber 412 is at least the threshold amount greater than the landfill temperature and/or whether the temperature of the landfill gas in the gas composition chamber is at least at the target temperature.

In some embodiments, the gas analyzer controller 419 may be configured to control the temperature control mechanism to generate heat using a heating element. In some embodiments, the heating element may comprise a resistive surface. In some embodiments, the gas analyzer controller 419 may be configured to control a current source that generates current in the resistive surface of the temperature control mechanism 418. For example, the gas analyzer controller may be configured to increase the generated current to cause the resistive surface to generate more heat. As a result of generating more heat, the resistive surface may cause temperature of the landfill gas in the gas composition chamber 412 to increase.

In some embodiments, the gas analyzer controller 419 may be configured to use input received from the temperature sensor 416A indicating a temperature of landfill gas in the gas composition chamber 412. In some embodiments, the gas analyzer controller 419 may be configured to control the temperature control mechanism 418 to heat landfill gas in the gas composition chamber such that the temperature sensor 416A indicates that the landfill gas in the chamber 412 has reached at least the target temperature. In some embodiments, the gas analyzer controller 419 may comprise a PID controller that controls the temperature control mechanism 418 to heat the landfill gas in the chamber 412 to the target temperature. In some embodiments, the gas analyzer controller 419 may be configured to control the temperature control mechanism to heat the landfill gas in the chamber 412 to at least at the target temperature. In some embodiments, the gas analyzer controller 419 may be configured to control the temperature control mechanism to hold the landfill gas in the chamber 412 at the target temperature or within a range of the target temperature. In some embodiments, the gas analyzer controller 419 may control the temperature control mechanism to prevent the temperature of the landfill gas from exceeding a certain temperature. For example, the gas analyzer controller 419 may control the temperature control mechanism to reduce the amount of heat generated by the temperature control mechanism to prevent the temperature of the landfill gas sample from exceeding a limit.

In some embodiments, when the gas analyzer controller 419 determines that the temperature of the landfill gas in the gas composition chamber 412 has reached at least the target temperature (e.g., based on a measurement obtained from the temperature sensor 416A), the gas analyzer controller 419 may be configured to control one or more gas characteristic sensors 414 to obtain one or more measurements for the characteristic(s). In some embodiments, the gas analyzer controller 419 may be configured to trigger the gas characteristic sensor(s) to take the measurement(s) when the gas analyzer controller 419 determines that the landfill gas in the gas composition chamber 412 is at least at the target temperature, or heated above the landfill temperature by the threshold temperature. For example, the gas analyzer controller 419 may be configured to receive a temperature measurement from the temperature sensor 416A and determine, based on the measurement, that the landfill gas in the gas composition chamber 412 has reached a target temperature (e.g., 55 degrees Celsius), or that the landfill gas has reached a temperature that is a threshold temperature greater than the landfill temperature (e.g., 25 degrees Celsius). When the gas analyzer controller 419 makes this determination, the gas analyzer controller 419 may be configured to trigger measurements by the gas characteristic sensor(s). For example, upon determining that a target temperature is met, the gas analyzer controller 419 may be configured to trigger a gas composition measurement by the gas characteristic sensor(s). The gas characteristic sensor(s) may be configured to measure concentration of one or more gases (e.g., methane, oxygen, nitrogen, carbon dioxide) in the landfill gas in the gas composition chamber 412.

FIG. 4B illustrates an example interaction between components of the gas analyzer 410. In some embodiments, the gas analyzer 410 can be modified to enable other interactions not illustrated by FIG. 4B. In some embodiments, the gas analyzer controller 419 may be configured to obtain measurements from the landfill temperature sensor 416B which the gas analyzer controller 419 may be configured to use to determine whether the temperature of landfill gas in the gas composition chamber 412 is a threshold temperature greater than the landfill temperature. In some embodiments, the gas analyzer controller 419 may be configured to not receive temperature measurements from the temperature sensor 416A indicating a temperature of landfill gas in the gas composition chamber 412. The gas analyzer controller 419 may be configured to control the temperature control mechanism 418 based on the target or threshold temperature received from the target temperature determination module 417 alone. In some embodiments, the temperature determination module 417 may comprise a subcomponent of the gas analyzer controller 419.

Furthermore, FIG. 4B illustrates exemplary sensors that may be part of the set of sensors in a gas analyzer 410. In some embodiments, the gas analyzer 410 may include other sensors not displayed in FIG. 4B. For example, the gas analyzer 410 may include a humidity sensor for measuring humidity of landfill gas in the gas composition chamber 412. In another example, the gas analyzer 410 may include one or more additional sensors for measuring environmental factors. Example sensors for measuring environmental factors are described herein.

Figure 5:
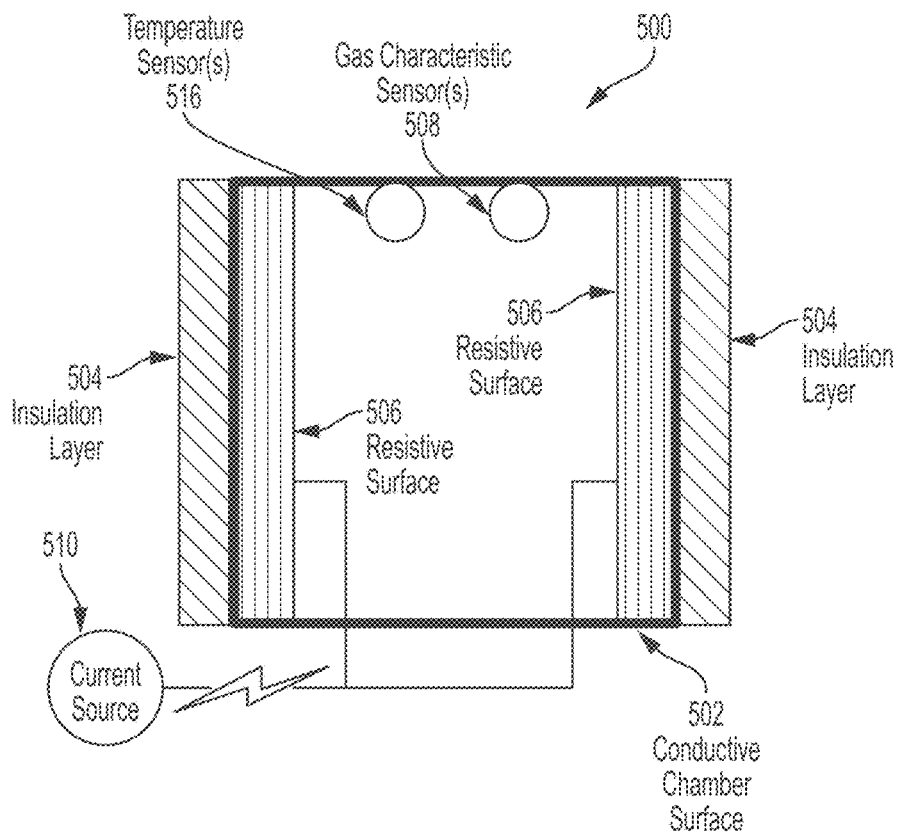
FIG. 5 shows components of an example temperature control mechanism, in accordance with some embodiments of the technology described herein.

FIG. 5 illustrates components of an example of a temperature control mechanism 500 in accordance with some embodiments of the technology described herein. The temperature control mechanism 500 may, for example, be used as the temperature control mechanism 418 in the gas analyzer 410 to heat landfill gas in gas composition chamber 412 described above with reference to FIG. 4.

In some embodiments, the temperature control mechanism 500 includes a heating element (e.g., a resistive surface(s)) 506 in a gas composition chamber in contact with a conductive chamber surface 502 of the gas composition chamber. In some embodiments, the resistive surface 506 may comprise a resistive surface placed in contact with the conductive chamber surface 502. The resistive surface may, for example, comprise carbon, a resistive metal, ceramic, or other type of resistive material. Embodiments are not limited to any particular type of resistive surface. The resistive surface(s) 506 may receive an electrical current from a current source 510. As a result of the electrical current, the resistive surface(s) 506 may generate heat. The generated heat may be conducted by the conductive chamber surface 502 of the gas composition chamber and absorbed by the landfill gas in the gas composition chamber resulting in the landfill gas increasing in temperature.

In some embodiments, the conductive chamber surface 502 may comprise a conductive metal such as aluminum, steel, silver, copper, gold, tungsten, iron, or other metal, or a combination of metals. Additionally or alternatively, the conductive surface 502 may comprise another type of conductive surface such as graphite, a conductive polymer, or other conductive material. Embodiments are not limited any particular type of conductive material as any suitable material may be used for the gas composition chamber surface 502.

Although embodiments of the temperature control mechanism are discussed herein with a resistive surface, some embodiments may be configured to use other types of heating elements in place of or in addition to a resistive surface. For example, the heating element may comprise a radiator, chemical reaction based heater, or other type of heating element as embodiments are not limited to a particular heating element.

In some embodiments, the temperature control mechanism 500 includes a current source 510 that may be configured to generate an electrical current that flows through the resistive surface(s) 506 to cause the resistive surface(s) 506 to generate heat. The current source may comprise an electrical circuit that generates the electrical current such as a voltage source in series with a resistor, a constant current diode, an operational amplifier circuit, or another other type of electrical circuit to generate an electrical current. In some embodiments, the current source may be connected to the resistive surface(s) 506 via an electrical circuit via which the electrical current may reach the resistive surface(s) 506. Increasing the electrical current may increase the amount of heat generated by the resistive surface(s) 506 while decreasing the electrical current may decrease the amount of heat generated by the resistive surface(s) 506. In some embodiments, a controller (e.g., gas analyzer controller 419 discussed above with reference FIGS. 4A-B) may be configured to control the electrical current level to adjust temperature of landfill gas in the gas composition chamber as described above with reference to FIG. 4.

In some embodiments, the current source 510 may be replaced or supplemented with another type of energy source. For example, the temperature control mechanism 500 may include a voltage source (e.g., a battery) in place of, as part of, or to supplement the current source 510 for generating a current in the resistive surface. In some embodiments, the temperature control mechanism 500 may include a solar heat energy source that absorbs heat from the sun to heat a heating element of the temperature control mechanism 500.

Although the current source 510 is shown outside of the gas composition chamber in the embodiment illustrated in FIG. 5, in some embodiments, the current source 510 may be placed in the gas composition chamber. In some embodiments, the current source 510 and the resistive surface(s) 506 may comprise a single piece of hardware that may be placed in the gas composition chamber. Embodiments are not limited to any particular location or placement of the current source 510.

In some embodiments, the temperature control mechanism 500 includes an insulation layer 504 around the conductive chamber surface 502. The insulation layer 504 may limit the amount of heat that escapes the gas composition chamber. By doing so, the landfill gas in the gas composition chamber may absorb more of the heat generated by the resistive surface(s) 506 during the heating process. The insulation layer 504 may further facilitate keeping the landfill gas at least at a target temperature for a period of time during which measurements of one or more characteristics of the landfill gas may be obtained. In some embodiments, the insulation layer 504 may comprise a thermal coating or jacket placed around the surface of the gas composition chamber 502. The coating or jacket may comprise insulative material such as plastic, aerogel, wool, poly urethane foam, polystyrene, cellulose, and/or any other type of insulation material that resists heat flow.

In some embodiments, the temperature control mechanism 500 includes one or more temperature sensors 516 configured to measure a temperature of landfill gas in the gas composition chamber. The temperature sensor(s) 516 may, for example, be operated by a controller (e.g., gas analyzer controller 419) to obtain measurements of the landfill gas temperature in the gas composition chamber, and to use the measurements to control heating of the landfill gas as described above with respect to FIG. 4B. For example, the controller may control the electrical current generated by the current source 510 based on the temperature measurements. The temperature sensor(s) 516 may comprise a thermocouple, a thermistor, a resistance temperature detector, a fiber-optic temperature probe, and/or any other type of temperature sensor capable of measuring a temperature of the landfill gas.

In some embodiments, the temperature sensor(s) 516 may include one or more temperature sensors for measuring a temperature of landfill gas in the landfill (e.g., a landfill temperature). Although the temperature sensor(s) 516 are shown in FIG. 5 as being in the gas composition chamber, in some embodiments, one or more of the temperature sensor(s) for measuring the landfill temperature may be placed outside of the gas composition chamber. For example, the temperature sensor(s) may be placed in a pipe upstream of the gas composition chamber through which a landfill gas sample may enter the gas composition chamber. In another example, the temperature sensor(s) for measuring the landfill temperature may be placed in a landfill gas extraction system upstream of the gas composition chamber where temperature of landfill gas may be measured prior to entering a gas analyzer. The temperature sensor(s) may be operated by a controller to obtain a measurement(s) of the landfill temperature, and used to control the heating of the landfill gas in the gas composition chamber (e.g., to a threshold temperature above the landfill temperature). Additionally or alternatively, the landfill temperature may be used to determine a target temperature or threshold temperature to heat the landfill gas in the gas composition chamber to as described above with reference to FIGS. 4A-B. The temperature sensor(s) for measuring the landfill temperature may comprise a thermocouple, a thermistor, a resistance temperature detector, a fiber-optic temperature probe, and/or any other type of temperature sensor capable of measuring a temperature of the landfill gas. Embodiments are not limited to any particular type of temperature sensor(s).

In some embodiments, the gas composition chamber includes one or more gas characteristic sensors 508 for measuring one or more characteristics of the landfill gas in the gas composition chamber. For example, when the gas composition chamber collects a sample of landfill gas in the gas composition chamber, a controller may operate the gas characteristic sensor(s) 508 to obtain measurements of the characteristic(s) of the sample of landfill gas in the gas composition chamber. In some embodiments, the gas characteristic sensor(s) may comprise one or more sensors for measuring a concentration of a gas in the landfill gas sample. Examples of gas characteristic sensor(s) are discussed herein.

In some embodiments, a gas analyzer (e.g., gas analyzer 410) may be configured to use measurements obtained using the gas characteristic sensor(s) 508 to determine an energy content of landfill gas being extracted from the landfill. In some embodiments, the sensor(s) 508 may measure the concentration of methane in the landfill gas. The gas analyzer 410 may be configured to determine the energy content of the landfill gas based on the measured concentration of methane in the landfill gas. For example, based on the concentration of methane in the landfill gas sample, the gas analyzer may be configured to determine an energy density and/or specific energy of landfill gas being extracted from the landfill.

Figure 6:
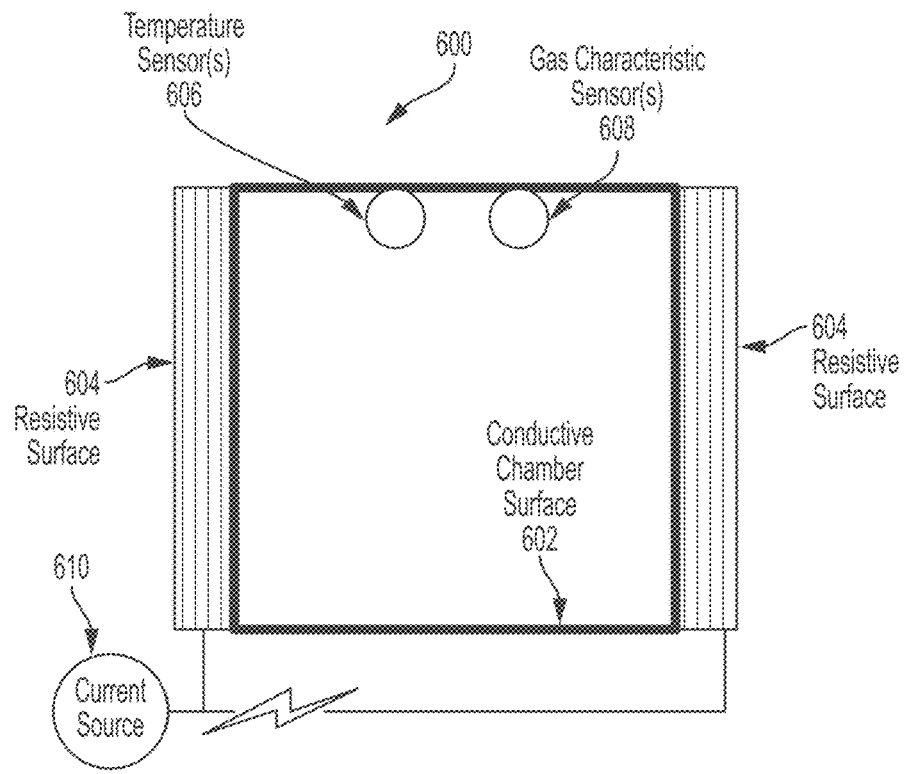
FIG. 6 shows components of another example temperature control mechanism, in accordance with some embodiments of the technology described herein.

FIG. 6 shows components of another example temperature control mechanism, in accordance with some embodiments of the technology described herein. For example, the temperature control mechanism 600 may be used as the temperature control mechanism 418 in the gas analyzer 410 to heat landfill gas in gas composition chamber 412 described above with reference to FIG. 4.

In some embodiments, the temperature control mechanism 600 includes a heating element (e.g., one or more resistive surfaces 604) in contact with a conductive chamber surface 602 of a gas composition chamber. In some embodiments, the resistive surface(s) 604 may comprise one or more resistive surfaces placed outside of the gas composition chamber in contact with a conductive chamber surface 602 of the gas composition chamber. The resistive surface(s) may, for example, comprise carbon, a resistive metal, ceramic, or other type of resistive material. Some embodiments are not limited to a particular material for the resistive surface(s) 604. The resistive surface(s) 604 may be configured to receive an electrical current from a current source 610. As a result of the electrical current, the resistive surface(s) 604 may generate heat. The generated heat may be conducted by the conductive chamber surface 602 of the gas composition chamber to the landfill gas in the gas composition chamber. The landfill gas may absorb the conducted heat and, as a result, increase in temperature.

In some embodiments, the conductive chamber surface 602 may comprise a conductive metal such as aluminum, steel, silver, copper, gold, tungsten, iron, or other metal, or a combination of metals. Additionally or alternatively, the conductive surface 602 may comprise another type of conductive surface such as graphite, a conductive polymer, or other conductive material.

Although in some embodiments the temperature control mechanism may include a resistive surface, other types of heating elements may be used in place of or in addition to a resistive surface. For example, the heating element may comprise a radiator, chemical reaction based heater, or other type of heating element.

In some embodiments, the temperature control mechanism 600 includes a current source 610 configured to generate an electrical current that flows through the resistive surface(s) 604 to cause the resistive surface(s) 604 to generate heat. The current source may comprise an electrical circuit that generates the electrical current such as a voltage source in series with a resistor, a constant current diode, an operational amplifier circuit, or another type of electrical circuit to generate an electrical current. In some embodiments, the current source may be connected to the resistive surface(s) 604 via an electrical circuit via which the electrical current may reach the resistive surface(s) 604. Increasing the electrical current may increase the amount of heat generated by the resistive surface(s) 604 while decreasing the electrical current may decrease the amount of heat generated by the resistive surface(s) 604. In some embodiments, a controller (e.g., gas analyzer controller 419 discussed above with reference FIGS. 4A-B) may control the electrical current level to adjust temperature of landfill gas in the gas composition chamber.

In some embodiments, the current source 610 may be replaced or supplemented with another type of energy source. For example, the temperature control mechanism 600 may include a voltage source (e.g., a battery) in place of, as part of, or to supplement the current source 610 for generating a current in the resistive surface. In some embodiments, the temperature control mechanism 600 may include a solar heat energy source that absorbs heat from the sun to heat a heating element of the temperature control mechanism 600.

Although the current source 610 is shown outside of the gas composition chamber in the embodiment illustrated in FIG. 6, in some embodiments, the current source 610 may be placed in the gas composition chamber. In some embodiments, the current source 610 and the resistive surface(s) 604 may comprise a single hardware component that may be placed in the gas composition chamber.

In some embodiments, the temperature control mechanism 600 includes one or more temperature sensors 606 with which are configured to measure a temperature of landfill gas in the gas composition chamber. The temperature sensor(s) 606 may, for example, be operated by a controller (e.g., gas analyzer controller 419) to obtain a measurement(s) of the landfill gas temperature in the gas composition chamber, and use the measurement(s) to control heating of the landfill gas as described above with respect to FIG. 4B. For example, the controller may be configured to control the electrical current generated by the current source 610 based on the temperature measurement(s). The temperature sensor(s) 606 may comprise a thermocouple, a thermistor, a resistance temperature detector, a fiber-optic temperature probe, and/or another type of temperature sensor capable of measuring the temperature of the landfill gas.

In some embodiments, the temperature sensor(s) 606 may include one or more temperature sensors for measuring a temperature of landfill gas in the landfill (e.g., a landfill temperature). Although the temperature sensor(s) 606 are shown in FIG. 6 as located in the gas composition chamber, in some embodiments, the temperature sensor(s) for measuring the landfill temperature may be placed outside of the gas composition chamber. For example, the temperature sensor(s) may be placed in a pipe upstream of the gas composition chamber through which a landfill gas sample may enter the gas composition chamber. In another example, the temperature sensor(s) for measuring the landfill temperature may be placed in a landfill gas extraction system upstream of the gas composition chamber where temperature of landfill gas may be measured prior to entering a gas analyzer. The temperature sensor(s) may be used by a controller to obtain a measurement(s) of the landfill temperature, and used to control the heating of the landfill gas in the gas composition chamber (e.g., to a threshold temperature above the landfill temperature). Additionally or alternatively, the landfill temperature may be used to determine a target temperature or threshold temperature to heat the landfill gas in the gas composition chamber to as described above with reference to FIGS. 4A-B. The temperature sensor(s) for measuring the landfill temperature may comprise a thermocouple, a thermistor, a resistance temperature detector, a fiber-optic temperature probe, and/or another type of temperature sensor capable of measuring a temperature of the landfill gas.

In some embodiments, the gas composition chamber includes one or more gas characteristic sensors 608 for measuring one or more characteristics of the landfill gas in the gas composition chamber. For example, when the gas composition chamber collects a sample of landfill gas in the gas composition chamber, a controller may be configured to operate the gas characteristic sensor(s) 608 to obtain a measurements of the characteristic(s) of the sample of landfill gas in the gas composition chamber. In some embodiments, the gas characteristic sensor(s) may comprise one or more sensors for measuring a concentration of a gas (e.g., oxygen, methane, nitrogen) in the landfill gas sample. Examples of sensors are discussed herein.

Although not illustrated in the embodiment illustrated in FIG. 6, in some embodiments, the temperature control mechanism 600 may include an insulation layer. The insulation layer may be placed on or around the resistive surface(s) 604. The insulation layer may prevent heat generated by the resistive surface(s) 604 from escaping and may ensure that heat generated by the resistive surface(s) 604 flows through the conductive chamber surface 602 to landfill gas in the gas composition chamber.

In some embodiments, a gas analyzer (e.g., gas analyzer 410) may be configured to use measurements obtained using the gas characteristic sensor(s) 608 to determine an energy content of landfill gas being extracted from the landfill. In some embodiments, the sensor(s) 608 may be configured to measure a concentration of methane in the landfill gas. The gas analyzer 410 may be configured to determine an energy content of the landfill gas based on the measured concentration of methane in the landfill gas. For example, based on the concentration of methane in the landfill gas sample, the gas analyzer may be configured to determine an energy density and/or specific energy of landfill gas being extracted from the landfill.

Figure 7A:
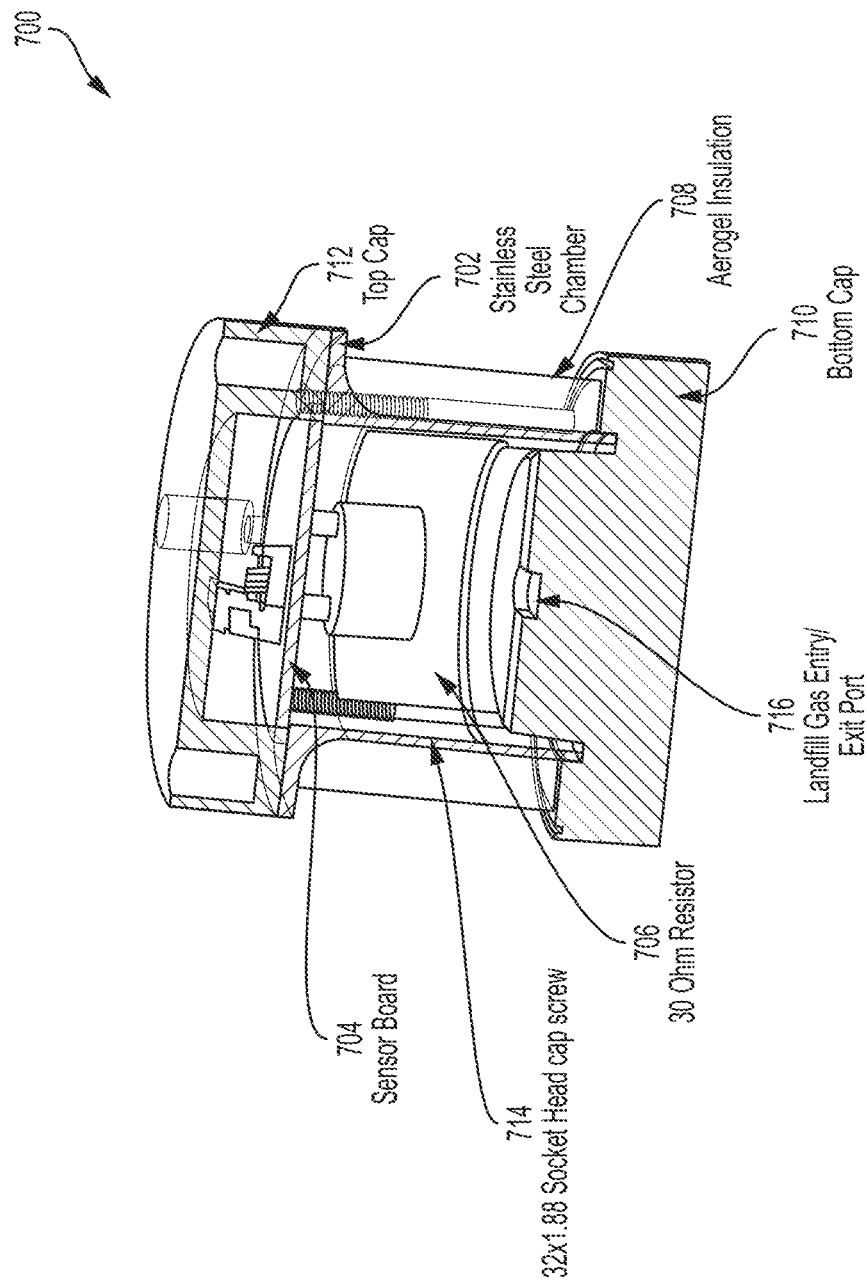
FIG. 7A is cutaway view of an example gas composition chamber, in accordance with some embodiments of the technology described herein.
Figure 7B:
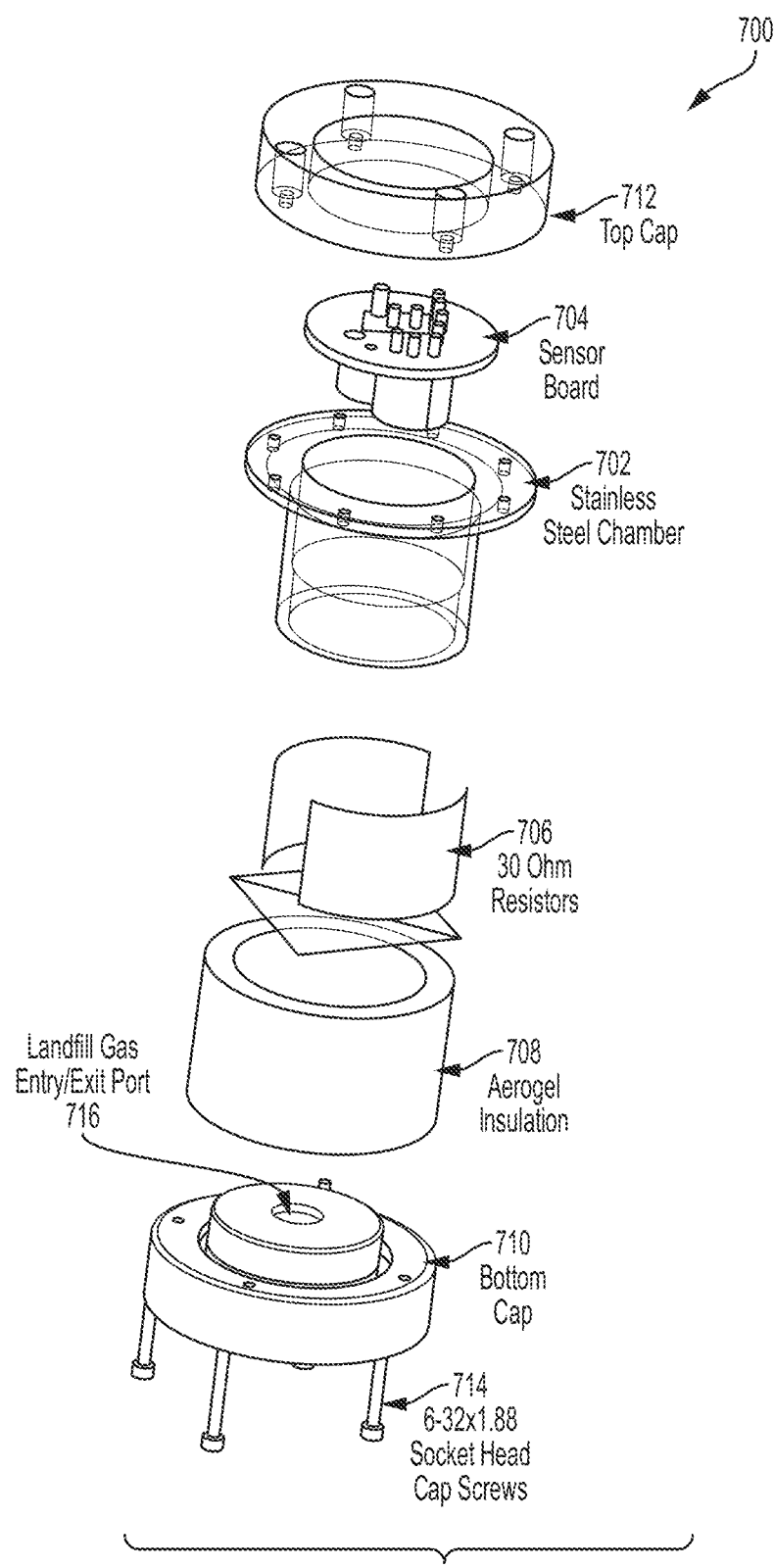
FIG. 7B is an exploded view of the example gas composition chamber shown in FIG. 7A, in accordance with some embodiments of the technology described herein.

FIG. 7A is cutaway view of an example gas composition chamber, in accordance with some embodiments of the technology described herein. FIG. 7B is an exploded view of the example gas composition chamber shown in FIG. 7A, in accordance with some embodiments of the technology described herein. The gas analyzer 700 includes a gas composition chamber 702 in which the gas analyzer 700 may be configured to collect a sample of landfill gas. The gas analyzer 700 includes a sensor board 704 holding one or more sensors for measuring one or more characteristics of the gas (e.g., temperature, composition, humidity). The chamber 702 is lined with a resistive surface (e.g., a resistor) 706. The gas analyzer 700 includes an insulation (e.g., aerogel insulation) 708 that surrounds an outer surface of the chamber 702.

In some embodiments, the resistors 706 may be configured to receive a current that causes the resistor to generate heat. The heat may be conducted by the chamber 702 and absorbed by the landfill gas resulting in the temperature of the landfill gas increasing. As described above with respect to FIGS. 5 and 6, the resistor 706 may comprise resistive material such as carbon, a resistive metal, ceramic, or other type of resistive material. Although the embodiment illustrated in FIG. 7 uses a 30 Ohm resistor, some embodiments may be configured to use a resistor having a different resistance. In some embodiments, the resistor may have a resistance of 5 Ohms, 10 Ohms, 15 Ohms, 20 Ohms, 25 Ohms, 30 Ohms, 35 Ohms, 40 Ohms, 45 Ohms, or 50 Ohms. In some embodiments, the resistor may have a resistance in a range between 1-100 Ohms, 1-50 Ohms, 10-100 Ohms, or 10-50 Ohms. In some embodiments, the resistor may have a resistance of at least 10 Ohms, 20 Ohms, 30 Ohms, 40 Ohms, or 50 Ohms.

In some embodiments, the chamber 702 may comprise a surface of conductive material. Example conductive materials for the surface of the chamber 702 are described herein. The chamber surface 702 in contact with the resistor 706 may allow heat generated by the resistor 706 to flow throughout the surface and to the landfill gas in the chamber 702. In this manner, the temperature of landfill gas in the chamber 702 may increase to a temperature that is sufficiently high to obtain accurate gas characteristic measurement(s) and prevent deterioration of the sensor(s).

In some embodiments, the insulation 708 surrounding the chamber 702 may prevent heat from flowing out of the chamber 702. This may result in more efficient heating of landfill gas in the chamber and reduce the amount of electric energy required to generate sufficient heat to cause the landfill gas to reach a target temperature. Examples of insulation material are discussed herein.

In some embodiments, the sensor board 704 may include a temperature sensor for measuring the temperature of landfill gas inside the gas composition chamber. Examples of temperature sensors that may be used are described herein. In some embodiments, the sensor board may comprise one or more gas characteristic sensors for measuring one or more characteristics of the landfill gas in the chamber 702. For example, the gas characteristic sensor(s) may comprise one or more sensors for measuring gas composition. In this example, the sensor(s) may obtain measurements of concentrations of one or more gases (e.g., methane, oxygen, carbon dioxide) in the landfill gas. In some embodiments, the sensor board 704 may comprise components of a controller configured to operate the sensor(s) and/or to operate temperature control mechanism. For example, the sensor board 704 may comprise components for controlling an electric current flowing through the resistor 706 to generate heat for heating the landfill gas in the chamber 702. In another example, the sensor 704 may comprise components for operating gas characteristic sensor(s) to obtain measurements of one or more characteristics of the landfill gas. The controller may be configured to determine when to trigger measuring of the characteristic(s) of the landfill gas (e.g., based on the temperature of the landfill gas in the chamber 702).

In some embodiments, the gas analyzer 700 includes a top cap 712 and a bottom cap 710 to seal the top and bottom of the chamber 702. In some embodiments, landfill gas may enter the gas chamber 702 via an entry/exit port 716. In some embodiments, the port 716 may be an opening into the chamber 702. In some embodiments, the port 716 may be coupled to a pipe that channels landfill gas to the chamber 702. In some embodiments, the caps may be configured to hold landfill gas within the chamber 702 and to prevent the landfill gas from escaping the chamber 702. In some embodiments, the gas analyzer 700 includes screws 714 for securing the bottom cap. The screws 714 may secure the cap in place such that the cap is sealed to contain the landfill gas. In some embodiments, the screws 714 may be configured to allow access to the chamber 702 for installation, maintenance, and/or troubleshooting. For example, the screws 714 may be removed to provide a user access to the chamber 702, resistors 706, insulation 708, sensor board 704, and other components in the gas analyzer 700 not illustrated.

Although FIGS. 7A-B illustrate a resistor 706 in the chamber 702 with an insulation 708, in some embodiments, the resistor 706 may be placed outside of the chamber 702. For example, the resistor 706 may be placed in contact with an outer surface of the chamber 702 as shown in FIG. 6.

Although FIGS. 7A-B illustrate an insulation 708, in some embodiments, the chamber 702 may not include an insulation 708. For example, as described above with reference to FIG. 6, the chamber 702 may have the resistor 706 placed outside of the chamber 702, and not include an insulation layer.

Figure 8:
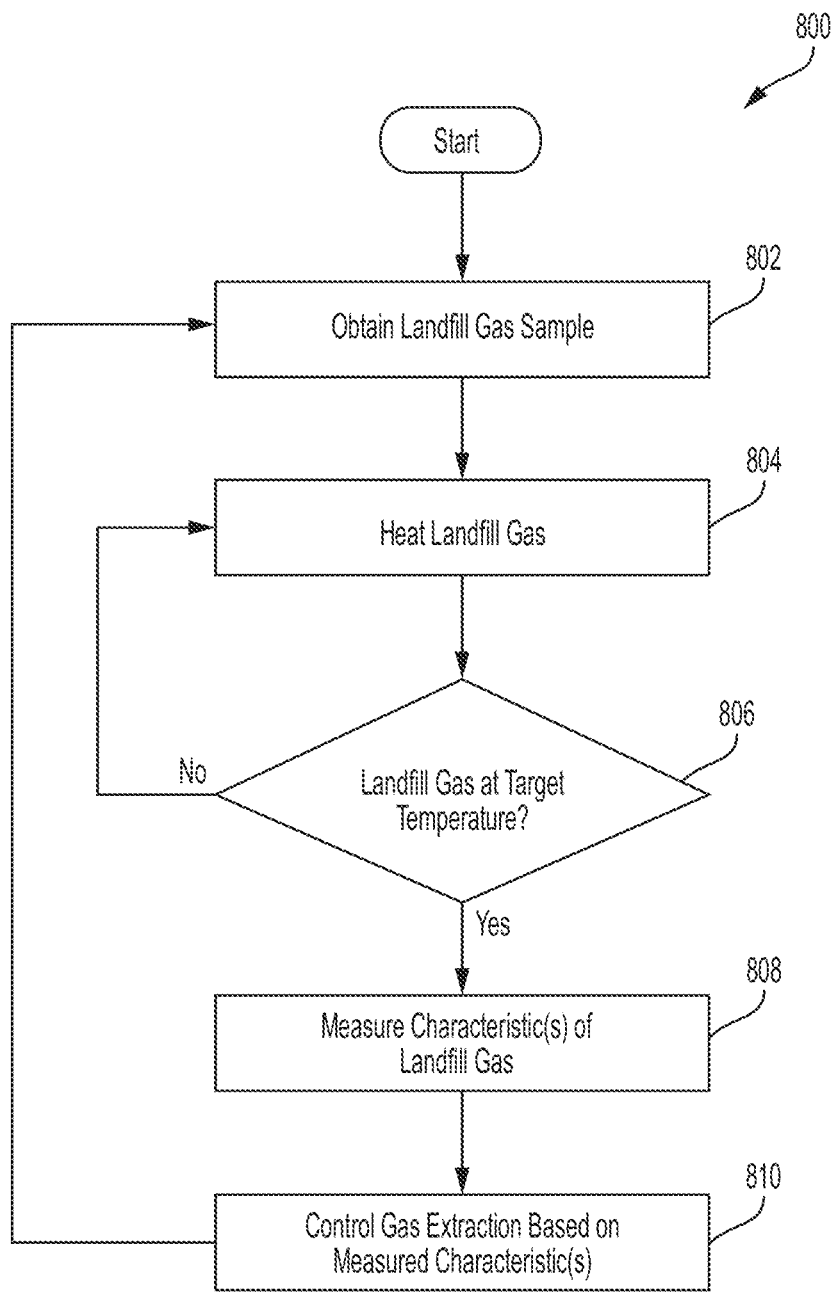
FIG. 8 is a flowchart of an illustrative process for controlling extraction of landfill gas, in accordance with some embodiments of the technology described herein.

FIG. 8 is a flowchart of an illustrative process for controlling extraction of landfill gas, in accordance with some embodiments of the technology described herein. The process 800 may be performed by any suitable system and/or computing device(s) and, for example, may be performed by control system 112 described above with reference to FIG. 1.

Process 800 begins at act 802, where the system executing process 800 (e.g., control system 112) obtains a sample of landfill gas. In some embodiments, the system may comprise a gas analyzer (e.g., gas analyzer 410 described above with reference to FIG. 1) that is configured to obtain the gas sample. The gas analyzer may include a gas composition chamber in which the gas analyzer may collect a sample of landfill gas from the landfill. In some embodiments, the system may be configured to control one or more valves and/or one or more pumps in order to extract a sample of landfill gas into the gas composition chamber (e.g., as described above with reference to FIG. 3). For example, the system may open a first vale and pump the landfill gas from a landfill gas channel of flow to the gas composition chamber via piping leading from the channel of flow to the gas composition chamber.

Next, process 800 proceeds to act 804, where the system heats the landfill gas. In some embodiments, the system may comprise a temperature control mechanism which the system may be configured to use to heat the obtained landfill gas sample. The temperature control mechanism may, for example, comprise a mechanism described in FIG. 5 or 6 above. For example, the system may be configured to generate an electric current that flows through one or more resistive surfaces placed in contact with the gas composition chamber. The electric current in the resistive surface(s) may cause the resistive surface(s) to generate heat which, in turn, may heat the landfill gas in the gas composition chamber. A conductive surface of the gas composition chamber may conduct the heat generated by the resistive surface(s) and allow it to flow to the landfill gas in the gas composition chamber.

Next, process 800 proceeds to act 806, where the system determines whether the landfill gas has reached a target temperature. In some embodiments, the target temperature may comprise a temperature that is a threshold temperature (e.g., 1, 10, 15, 20, or 25 degrees Celsius) above a temperature of landfill gas in the landfill (e.g., landfill temperature). The system may include one or more temperature sensors (e.g., in the gas composition chamber) for measuring the temperature of the obtained landfill gas. The system may be configured to obtain measurements from the sensor(s) and to use the obtained measurements to determine whether the landfill gas sample has met the target temperature. In some embodiments, the system may further include one or more other sensors for measuring the landfill temperature. The system may be configured to use measurements of the landfill temperature to determine whether the obtained gas sample is at a target temperature (e.g., a temperature that is at least the threshold temperature above the landfill temperature).

In some embodiments, the system may be configured to determine the target temperature (e.g., the threshold temperature above the landfill temperature) based on environmental factors. In some embodiments, the system may be configured to determine the target temperature based on an ambient temperature of the environment. For example, the system may be configured to determine a lower target temperature for the landfill gas sample in a winter season when the ambient temperature is colder than in a summer season when the ambient temperature is warmer. In this manner, the system may reduce the amount of heating necessary to heat the obtained landfill gas sample to the target temperature.

If, at 806, the system determines that the landfill gas temperature has not reached the target temperature, process 800 returns to act 804, where the system continues heating the obtained landfill gas sample. In some embodiments, the system may include a controller (e.g. a PID controller) with which the system controls the temperature control mechanism (e.g., controls a current) to heat the landfill gas to the target temperature. In some embodiments, the system may control the temperature control mechanism to maintain the landfill gas at a temperature greater than or equal to the target temperature (e.g., 1, 10, or 25 degrees Celsius above the landfill temperature). In some embodiments, the system may control the temperature control mechanism to prevent the temperature of the landfill gas from exceeding a temperature (e.g., 55, 60, 65, 70, or 75 degrees Celsius).

If, at act 806, the system determines that the landfill gas is at least at the target temperature, process 800 proceeds to act 808. In some embodiments, the system may be configured to use one or more temperature sensors to determine whether the landfill gas is at least at a target temperature value or exceeds the landfill temperature by the target threshold amount (e.g., 1, 10, or 25 degrees Celsius). In some embodiments, the system may be configured to determine whether the landfill gas has maintained a temperature of at least the target temperature for a period of time (e.g., 10 seconds, 5 minutes, 1 hour).

At act 808, the system measures one or more characteristics of the landfill gas. In some embodiments, the system may include one or more gas characteristic sensors with which the system may obtain measurements of the characteristic(s). The system may be configured to operate the characteristic sensor(s) to obtain the measurements. For example, the system may be configured to measure a gas composition measurement of the landfill gas. In this example, the system may be configured to measure a concentration of one or more gases in the landfill gas (e.g., methane, oxygen, carbon dioxide, or nitrogen). The system may further use the measured concentration of methane to determine the energy content of landfill gas being extracted through the landfill gas extraction system. In some embodiments, the system may additionally or alternatively measure one or more other characteristics of the landfill gas such as humidity, pressure, and/or other characteristic.

Next, process 800 proceeds to act 810 where the system controls gas extraction through the gas extraction system based on the measured characteristic(s) of the landfill gas. In some embodiments, the system may be configured to control one or more parameters of the gas extraction system such as a flow rate. In some embodiments, the system may be configured to control a flow control mechanism (e.g., one or more valves) which controls the flow rate of gas extracted from landfill by the gas extraction system as described above with reference to FIG. 4.

In some embodiments, the system may be configured to determine settings of the control parameter(s) based on the measured characteristic(s). In some embodiments, the system may be configured to determine an energy content of landfill gas being extracted from the landfill. The system may be configured to control gas extraction based on the measured energy content. In some embodiments, the system may be configured to determine a target energy content, and compare the measured energy content to the target energy content. If the determined energy content of the landfill gas is different from the target energy content, the system may control the parameter(s) (e.g., flow rate) to change the energy content. For example, to increase the energy content, the system may change a valve position of the flow control mechanism to increase the flow rate thereby increasing the energy content of the landfill gas being extracted by the gas extraction system. In some embodiments, the system may use one or more other measured characteristics to control flow rate. In some embodiments, the system may determine settings for one or more other control parameters such as pressure, temperature, or composition of landfill gas being extracted by the gas extraction system.

In some embodiments, the system may be configured to maintain the energy content of the landfill gas being extracted at the target energy content or within a range of the target energy content. For example, the system may include a PID controller that determines settings of the control parameter(s) to maintain the energy content of the landfill gas at the target energy content. In some embodiments, the system may be configured to determine a flowrate of landfill gas being extracted from the landfill that may attain and/or maintain the target energy content. For example, the system may input a target flowrate that may attain the target energy content as an input to the PID controller which, in turn, may control positions of one or more valves to achieve the target flowrate.

Heated Landfill Gas Well Piping

The inventors have recognized that the temperature outside of a landfill may drop over a period of time and cause liquid in well piping of a gas extraction system to freeze inside the well piping. The frozen liquid may obstruct flow of landfill gas through the well piping. For example, water in the well piping may freeze and prevent flow of landfill gas through the well piping. As another example, water may freeze around a manually controlled valve disposed in the well piping and obstruct flow of landfill gas through the valve opening. As yet another example, the freezing of liquid in the well piping may further affect an ability of a downstream control system to control flow of landfill gas through the well piping.

Some embodiments of the technology described herein provide for a system that heats a portion of well piping of a gas extraction system to prevent freezing of liquid in the well piping. The gas extraction system includes a vacuum source, and a well coupled to the vacuum source through the well piping. The system for heating the well piping includes a temperature sensor for measuring a temperature of a portion of the well piping that is disposed between the well, and a control system that controls the flow of landfill gas through the well piping. The system further includes a heating device for heating the portion of the well piping, and a controller that controls the heating device. The controller obtains a temperature of the portion of the well piping from the temperature sensor, and determines whether the temperature of the portion of the well is less than a threshold temperature. If the controller determines that the temperature is less than the threshold temperature, the controller controls the heating device to heat the portion of the well piping. Accordingly, the system heats the portion of the well piping to prevent liquid from freezing inside the well piping.

Some embodiments include insulation for insulating a portion of well piping of a gas extraction system. The insulation may facilitate in retaining heat in the well piping, and make heating of the portion of well piping more efficient. For example, an insulative jacket that covers the portion of well piping may reduce the rate at which heat generated by a heating device dissipates from the portion of well piping.

Figure 9:
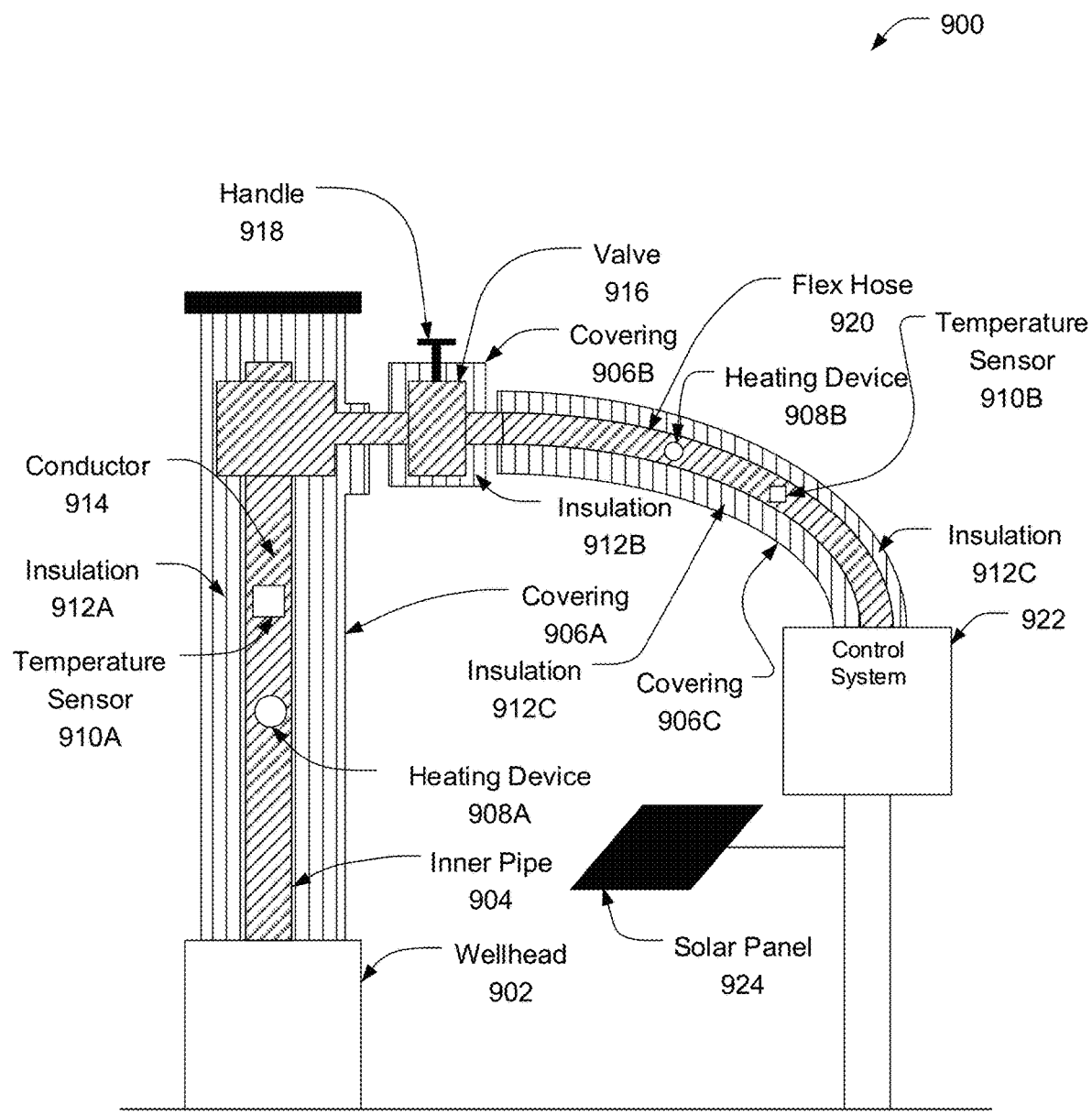
FIG. 9 illustrates components of an example system 900 for heating well piping of a gas extraction system, in accordance with some embodiments of the technology described herein.

FIG. 9 illustrates components of an example system 900 for heating a portion of well piping of a gas extraction system, in accordance with some embodiments of the technology described herein. The portion of the well piping includes an inner pipe 904 between a wellhead 902 and a manually controlled valve 916. The portion of well piping further includes a flex hose 920 that connects the manually controlled valve 916 to a control system 922 for controlling flow of landfill gas through the well piping. In some embodiments, the control system 922 may be control system 112 described above with reference to FIGS. 1A-C. Landfill gas flows from a gas extraction well up through the wellhead 902, inner pipe 904, manually controlled valve 916, flex hose 920, and the control system 922. After the landfill gas flows through the portion of well piping and the control system 922, it may flow through additional well piping to a gas output such as gas collection system 114 described above with reference to FIG. 1A.

In some embodiments, the inner pipe 904 may be a polyvinyl chloride (PVC) piping or polyethylene piping. In some embodiments, the inner pipe 904 may be metallic piping. For example, the inner pipe 904 may be copper, steel, aluminum, and/or iron piping. Although inner pipe 904 is illustrated as a single pipe, in some embodiments the inner pipe 904 may be formed from multiple pipes.

In some embodiments, the flex hose 920 may be a nylon, rubber, foam, and/or silicone hose. In some embodiments, the flex hose 920 may be a flexible PVC, and/or flexible plastic pipe. Some embodiments are not limited to a specific material for flex hose 920. Although the flex hose 920 is shown as a single hose, in some embodiments the flex hose 920 may be formed from multiple hoses and/or pipes.

In the illustrative embodiment of FIG. 9, the system 900 includes temperature sensors 910A-B, heating devices 908A-B, insulation 912A-B, and conductors 914A-B. Each of the heating devices 908A-B is configured to generate heat for heating a respective section of the portion of the well piping. Heating device 908A is configured to heat the inner pipe 904 and heating device 908B is configured to heat the flex hose 920. In some embodiments, a controller may be configured to control each of the heating devices 908A-B to heat the portion of well piping. The controller may be configured to control the heating devices based on temperature measurements received from temperature sensors 910A-B. Each of the temperature sensors 910A-B is configured to measure a temperature of a section of the portion of the well piping. Temperature sensor 910A is configured to measure a temperature of the inner pipe 904 and temperature sensor 910B is configured to measure a temperature of the flex hose 920. In some embodiments, a temperature sensor may be a thermocouple, a thermistor, a resistance temperature detector, a fiber-optic temperature probe, and/or another type of temperature sensor.

In some embodiments, the system 900 may have a single heating device configured to heat the portion of well piping and a single temperature sensor configured to measure a temperature of the portion of well piping. For example, the system 900 may include only (1) one of heating devices 908A or 908B, and (2) only one of temperature sensors 910A or 910B. A controller may be configured to control the single heating device based on a temperature of the portion of well piping received from the single temperature sensor. In some embodiments, the system 900 may have one heating device, two heating devices, three heating devices, or more heating devices. Some embodiments are not limited to a number of heating devices. In some embodiments, the system 900 may have one temperature sensor, two temperature sensors, three temperature sensors, or more temperature sensors. Some embodiments are not limited to a number of temperature sensors.

In the illustrative embodiment of FIG. 9, the system 900 includes a conductor 914 as illustrated by the slanted lines on the portion of the well piping to distribute heat generated by heating device 908A-B throughout the portion of the well piping. When the heating devices 908A-B generate heat, the conductor 914 may distribute the heat throughout the portion of well piping to maintain or raise a temperature inside the portion of the well piping. In some embodiments, the conductor may be heat tape that is adhered to the portion of the well piping. In some embodiments, the conductor 914 may be a metallic conductor that distributes heat throughout the portion of the well piping. For example, the conductor 914 may be copper or aluminum, or stainless steel, that covers the portion of well piping.

In the illustrative embodiment of FIG. 9, the system 900 includes insulation 912A-C for insulating the portion of well piping. The insulation may prevent the portion of the well piping from losing heat to the atmosphere. Although insulation 912A, 912B, and 912C are illustrated as separate insulation components, in some embodiments, insulation 912A, 912B, and 912C may form sections of a single insulative covering. For example, the insulative covering may be a jacket that coats sections of the portion of well piping. In some embodiments, each of the insulation 912A, 912B, and 912C may be separate components that insulate a respective section of the portion of well piping.

In the illustrative embodiment of FIG. 9, the system 900 includes covering 906A, 906B, and 906C for covering portions of the well piping. Although covering 906A, 906B, and 906C are illustrated as separate components, in some embodiments, covering 906A, 906B, and 906C may be portions of a single cover. For example, the cover may be a jacket or other coating that covers the portion of the well piping. In some embodiments, the insulation 912A-C may be part of the cover. For example, the covering may be an insulative jacket that covers the portion of the well piping to reduce the amount of heat that leaves the portion(s) of the well piping. The covering may be an aerogel, foam, polymer, plastic, aerogel, and/or other insulative material that covers the portion of well piping. In some embodiments, the cover may be fastened around the well piping. For example, the cover may be zip tied at different points of the portion of well piping. As another example, the cover may be fastened using metal fasteners. As yet another example, the cover may include a zipper that can be zipped up to fasten the cover around the portion of well piping. As yet another example, the cover may include a hook and loop fastener system to secure the cover around a surface of the portion of the well piping.

In some embodiments, each of covering 906A, 906B, and 906C may be separate components that cover respective sections of the portion of well piping. In some embodiments, the covering 906A may be an outer pipe that covers the inner pipe 904 of the well piping. The outer pipe may be installed around the inner pipe 904. For example, the outer pipe may be a polyvinyl chloride (PVC) pipe that covers the inner pipe 904 of the portion of well piping. The insulation 912A may be placed in a space between the outer pipe and the inner pipe 904. In some embodiments, the insulation 912A may be pour-in foam that is poured into the space between the inner pipe 904 and the outer pipe.

In some embodiments, the covering 906B may be a box that is placed around an enclosure of the valve 616. Insulation 912B may be placed in a space between the enclosure of the valve and the box to insulate the valve. In some embodiments, the insulation 912B may be pour-in foam that is poured in to the space between the box and the enclosure of the valve 916. The covering 906B may be installed around a handle 918 that is used to manually control the valve 916 such that the handle 918 is still exposed for access.

In some embodiments, each of the heating devices 908A-B include a resistive element. The resistive element may be configured to generate heat when an electrical current is applied to the resistive heating element. The heat may then be distributed by the conductor 914 throughout the portion of well piping. In some embodiments, a controller may be configured to control an electrical current that is applied to the resistive heating element. In some embodiments, the resistive element may include a polyimide. For example, the resistive element may be a polyimide sheet that is attached to the portion of well piping. In some embodiments, the resistive element may include carbon, a resistive metal, a ceramic, or other type of resistive material. Some embodiments are not limited to a particular type of resistive material.

In some embodiments, the heating devices 908A-B may each include a battery for powering the heating device. A heating device may be configured to use the battery to generate a current that is applied to a resistive heating element of the heating device to heat the portion of well piping. In some embodiments, the battery may be a lead acid battery. In some embodiments, the battery may be a rechargeable battery. In the illustrative embodiment of FIG. 9, the system 900 includes a solar panel 924 that may be configured to charge one or more batteries used by heating devices 908A-B. In some embodiments, the system 900 may be configured to charge the battery when the battery is not being used to power a heating device. In some embodiments, the solar panel 924 may include a controller configured to control charging of a battery by the solar panel 924. For example, the solar panel controller may determine when a battery is depleted of charge and, in response, trigger charging of the battery.

Figure 10:
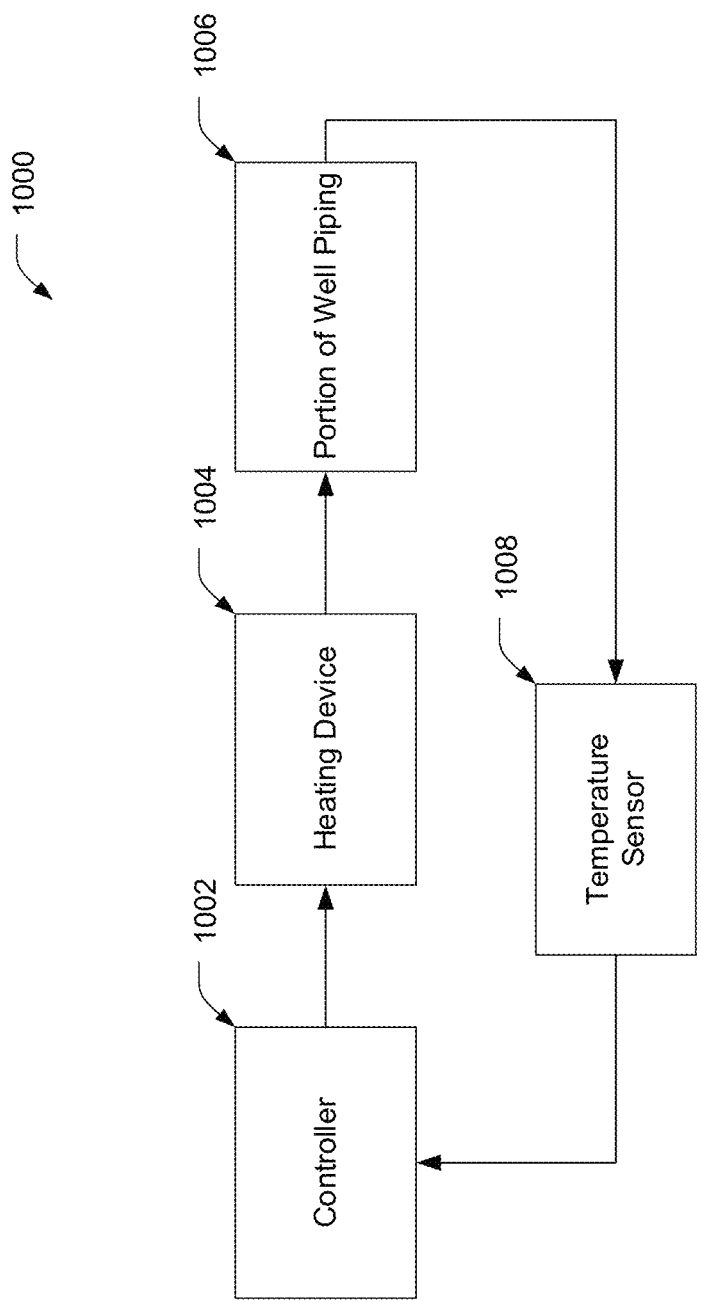
FIG. 10 is a block diagram illustrating example interactions among components of a system 1000 for heating well piping of a landfill gas extraction system, in accordance with some embodiments of the technology described herein.

FIG. 10 is a block diagram illustrating example interactions among components of a system 1000 for heating a portion of well piping, in accordance with some embodiments of the technology described herein. As shown in FIG. 10, the system 1000 includes a controller 1002 that is configured to control a heating device 1004. The heating device 1004 may be any suitable heating device such as, for example, heating device 908A or 908B described above with reference to FIG. 9. The heating device 1004 is configured to heat the portion of well piping 1006. The controller 1002 is configured to obtain a temperature of the portion of well piping from a temperature sensor 1008. The temperature sensor 1008 may be any suitable temperature sensor such as, for example, temperature sensor 910A or 910B described above with reference to FIG. 9. The controller 1002 may be configured to use the received temperature to control the heating device 1004. In some embodiments, the controller 1002 may be configured to determine whether the temperature of the portion of well piping 1006 meets a threshold temperature. The controller 1002 may be configured to control the heating device 1004 to generate heat if the controller 1002 determines that the temperature of the portion of well piping does not meet the threshold temperature.

In some embodiments, the controller 1002 may be configured to control the heating device 1004 by turning the powering the heating device on or off. For example, if the controller 1002 determines that the temperature of the portion of well piping does not meet a threshold temperature, the controller 1002 may power on the heating device 1004. As another example, if the controller 1002 determines that the temperature of the portion of well piping meets a threshold temperature, the controller 1002 may power off the heating device 1004.

In some embodiments, the controller 1002 may be configured to control the heating device 1004 by controlling an electrical current that flows through the heating device. For example, the heating device may include resistive heating element (e.g., a polyimide) that generates heat when electrical current flows through it. The controller 1002 may be configured to modulate the current that flows through the resistive heating element. In some embodiments, the controller 1002 may be configured to control the current by controlling a voltage that is applied to the resistive heating element. In some embodiments, the controller 1002 may be configured to select from multiple discrete voltage settings. In some embodiments, the controller 1002 may be configured to adjust voltage over a continuous range that can be applied to the resistive heating element.

In some embodiments, the controller 1002 may be co-located with the portion of well piping 1006. For example, the controller may be embedded as a component of the control system 922 described above with reference to FIG. 9. The controller 1002 may be physically connected to the heating device 1004 and temperature sensor 1008. For example, the controller 1002 may be connected to the heating device 1004 and/or the temperature sensor 1008 using wires. In some embodiments, the controller 1002 may be located at the portion of well piping, but configured to wirelessly communicate with the heating device 1004 and/or temperature sensor 1008.

In some embodiments, the controller 1002 may be remote from the portion of well piping. The controller 1002 may be configured to receive temperature readings from the temperature sensor 1008, and transmit a control input to the heating device 1004. In some embodiments, the controller 1002 may be configured to communicate with the heating device 1004 and the temperature sensor 1008 wirelessly. The temperature sensor 1008 may include a transmitter for wirelessly transmitting temperature readings to the controller 1002. The heating device 1004 may include a receiver for wirelessly receiving control inputs from the controller 1002. For example, the heating device 1004 may receive a voltage setting from the controller 1002, and/or a binary on/off command. In some embodiments, the receiver and transmitter may be a single transceiver. In some embodiments, the controller 1002 may be configured to communicate with the temperature sensor 1008 and heating device 1004 over a wireless network connection. For example, the system 1000 may include a network interface device co-located with the portion of well piping 1006 that implements the receiver and transmitter. The network device may be configured to transmit temperature data to the controller 1002, and receive control input data from the controller 1002.

In some embodiments, the controller 1002 may be implemented on a computing device with one or more processors and a storage medium. The computing device may include a network interface device via which the controller 1002 can communicate with components of the system 1000 located at a gas extraction system.

In some embodiments, the system 1000 may be configured to transmit diagnostic data to the controller 1002. For example, the system 1000 may transmit information about a charge level of a battery used to power the heating device 1004. The controller 1002 may be configured to use the diagnostic information to adjust one or more control inputs to the heating device 1004, and/or generate maintenance alerts or instructions for users.

Figure 11:
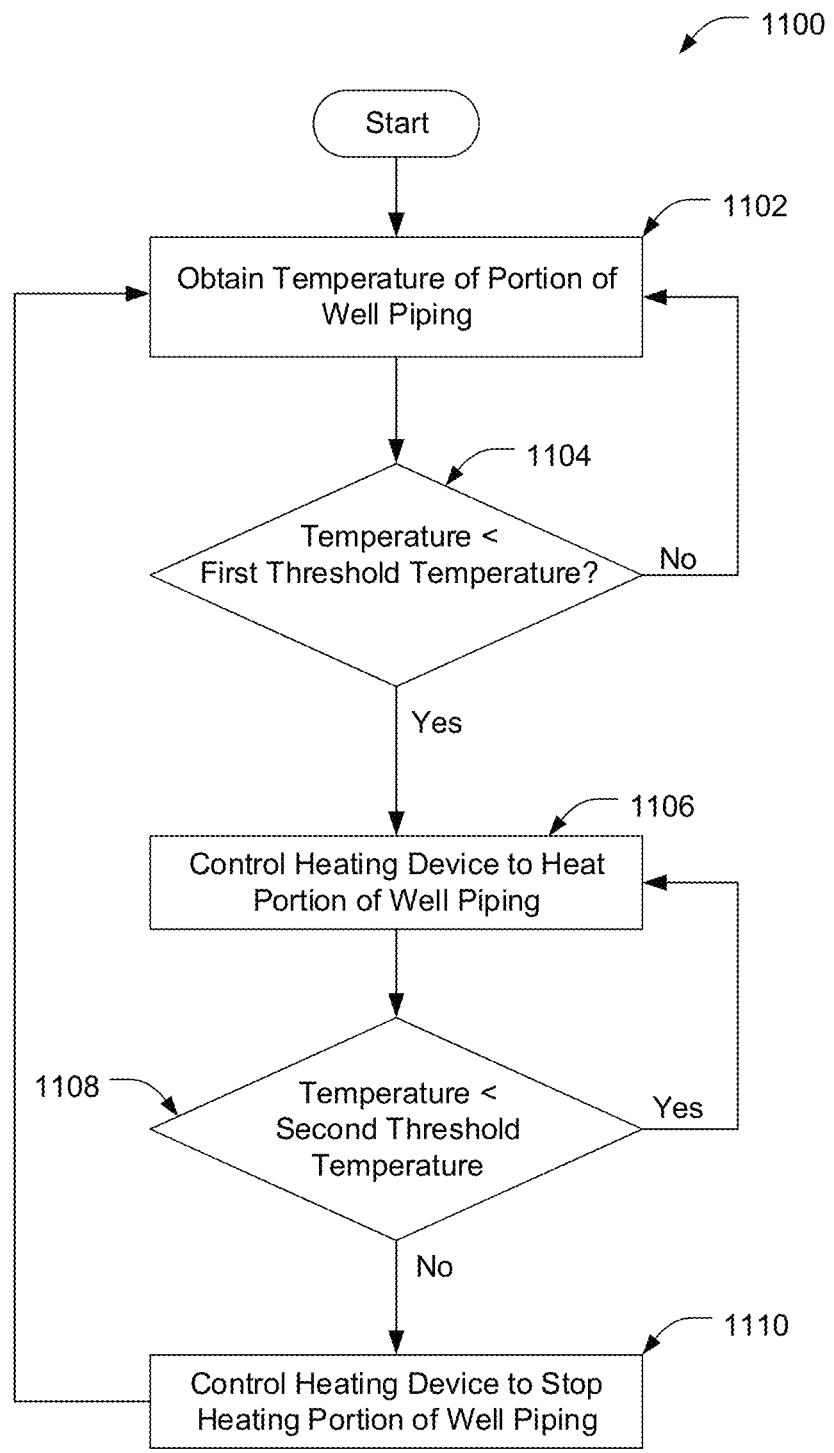
FIG. 11 is a flowchart of an illustrative process 1100 for heating well piping of a landfill gas extraction system, in accordance with some embodiments of the technology described herein.

FIG. 11 is a flowchart of an illustrative process 1100 for heating a portion of well piping, in accordance with some embodiments of the technology described herein. The process 1100 may be performed by controller 1002 described above with reference to FIG. 10.

Process 1100 begins at act 1102, where the system performing process 1100 obtains a temperature of the portion of well piping. The temperature may be measured by a temperature sensor. For example, the temperature may be measured by one of temperature sensors 910A-B described above with reference to FIG. 9. In some embodiments, the system may be configured to receive the temperature of the portion of well piping at regular intervals. For example, a system may receive the temperature every second, minute, hour, 5 hours, 10 hours, hours, 24 hours, or other period. In some embodiments, the system may be configured to receive the temperature in response to a command or trigger. For example, the system may ping a temperature sensor to take a measurement and/or to transmit a temperature reading. The system may receive the temperature in response to the command or trigger.

Next, process 1100 proceeds to act 1104 where the system determines whether the obtained temperature is less than a first threshold temperature. In some embodiments, the first threshold temperature may be a temperature at which liquid in the portion of well piping freezes. For example, the threshold temperature may be a temperature at which water in the well piping will freeze. In some embodiments, the first threshold temperature is −15, −10, −5, 0, 5, 10, or 15 degrees Celsius. If at act 1104 the system determines that the temperature is not less than the first threshold temperature, then process 1100 proceeds to act 1102 where the system obtains the temperature of the portion of well piping.

If at act 1104 the system determines that the temperature is less than the first threshold temperature, then process 1100 proceeds to act 1106 where the system controls a heating device to heat the portion of well piping. For example, the system may be configured to control heating devices 908A-B described above with reference to FIG. 9. In some embodiments, the system may be configured to turn the heating device on. In some embodiments, the system may be configured to control an electrical current that is applied to a resistive heating element of the heating device.

Next, process 1100 proceeds to act 1108 where the system determines whether the temperature of the portion of well piping is less than the second threshold temperature. In some embodiments, the system may be configured to obtain another temperature reading of the temperature of the portion of well piping prior to determining whether the temperature of the portion of well piping is less than the second threshold temperature. In some embodiments, the second threshold temperature may be a temperature at which liquid would not freeze in the portion of well piping. For example, the second threshold temperature may be a temperature at which water would not freeze, and at which frozen water would melt. In some embodiments, the second threshold temperature is 10, 15, 20, 25, or 30 degrees Celsius. If at act 1108 the system determines that the temperature of the portion of well piping is less than the second threshold temperature, then process 1100 proceeds to act 1106 where the system continues to control the heating device to heat the portion of well piping. In some embodiments, the system may be configured to keep the heating device on. In some embodiments, the system may be configured to modulate a setting of the heating device. For example, the system may increase a voltage and/or an electrical current being applied to a resistive heating element of the heating device.

If at act 1108 the system determines that the temperature of the portion of well piping exceeds the second threshold temperature, then process 100 proceeds to act 1110 where the system controls the heating device to stop heating the portion of well piping. In some embodiments the system may be configured to stop the heating device from generating heat. For example, the system may power off the heating device. In some embodiments, the system may be configured to incrementally reduce an amount of heat being generated by the heating device. For example, the system may incrementally reduce a voltage and/or an electrical current flowing through a resistive heating element of the heating device.

After controlling the heating device to stop heating the portion at act 1110, process 1100 returns to act 1102 where the system obtains a temperature of the portion of well piping.

Various features and aspects of the present disclosure may be used alone, in any combination of two or more, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The terms "approximately", "substantially," and "about" may be used to mean within ±20% of a target value in some embodiments, within ±10% of a target value in some embodiments, within ±5% of a target value in some embodiments, and within ±2% of a target value in some embodiments. The terms "approximately" and "about" may include the target value.

Also, the concepts disclosed herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

What is claimed is:

1. A control system comprising:
   a chamber;
   a temperature sensor, disposed in the chamber, for measuring temperature of a sample of landfill gas extracted from a landfill;
   a gas characteristic sensor, disposed in the chamber and different from the temperature sensor, for measuring a gas composition of the sample of landfill gas; and
   at least one controller configured to perform a method for reducing deterioration of the gas characteristic sensor, the method comprising:
      while the sample of landfill gas is in the chamber:
         obtaining, from the temperature sensor, a measurement of the temperature of the sample of landfill gas;
         responsive to determining, using the measurement of the temperature of the sample of landfill gas, that the temperature of the sample of landfill gas is greater than or equal to a target temperature, operating the gas characteristic sensor to take at least one new measurement of the gas composition of the sample of landfill gas; and
         responsive to determining, using the measurement of the temperature of the sample of landfill gas, that the temperature of the sample of landfill gas is not greater than or equal to the target temperature, adjusting the temperature of the sample of landfill gas in the chamber.

2. The control system of claim 1, wherein, when it is determined that the temperature of the sample of landfill gas is not greater than or equal to the target temperature, adjusting the temperature of the sample of landfill gas comprises increasing the temperature of the sample of landfill gas by heating the sample of landfill gas.

3. The control system of claim 1, wherein the at least one controller is further configured to:
   subsequent to adjusting the temperature of the sample of landfill gas, obtain a second measurement of the temperature of the sample of landfill gas while the sample of landfill gas is in the chamber; and
   determine whether the second measurement of the temperature of the sample of landfill gas is greater than or equal to the target temperature.

4. The control system of claim 1, wherein adjusting the temperature of the sample of landfill gas comprises adjusting the temperature of the sample of landfill gas using a heating element.

5. The control system of claim 1, wherein adjusting the temperature of the sample of landfill gas comprises adjusting the temperature of the sample of landfill gas using a resistive surface configured to generate heat as a result of electric current flowing through the resistive surface.

6. The control system of claim 1, wherein the gas characteristic sensor comprises an infrared sensor.

7. The control system of claim 1, wherein the gas characteristic sensor comprises an electrochemical sensor.

8. The control system of claim 1, wherein obtaining the measurement of the temperature of the sample of landfill gas comprises controlling the temperature sensor to obtain the measurement of the temperature of the sample of landfill gas.

9. The control system of claim 1, wherein obtaining the measurement of the temperature of the sample of landfill gas comprises receiving the measurement of the temperature of the sample of landfill gas from at least one second controller configured to control the temperature sensor to obtain the measurement of the temperature of the sample of landfill gas.

10. A method for reducing deterioration of a gas characteristic sensor, the method comprising:
    performing, with at least one controller:
       while a sample of landfill gas extracted from a landfill is in a chamber:
          obtaining, from a temperature sensor disposed in the chamber, a measurement of a temperature of the sample of landfill gas;
          responsive to determining, using the measurement of the temperature of the sample of landfill gas, that the temperature of the sample of landfill gas is greater than or equal to a target temperature, operating a gas characteristic sensor to take at least one new measurement of gas composition of the sample of landfill gas; and
          when it is determined that the temperature of the sample of landfill gas is not greater than or equal to the target temperature, adjusting the temperature of the sample of landfill gas.

11. The method of claim 10, wherein, when it is determined that the temperature of the sample of landfill gas is not greater than or equal to the target temperature, adjusting the temperature of the sample of landfill gas comprises increasing the temperature of the sample of landfill gas by heating the sample of landfill gas.

12. The method of claim 10, further comprising:
    subsequent to adjusting the temperature of the sample of landfill gas, obtaining a second measurement of the temperature of the sample of landfill gas while the sample of landfill gas is in the chamber; and
    determining whether the second measurement of the temperature of the sample of landfill gas is greater than or equal to the target temperature.

13. The method of claim 10, wherein adjusting the temperature of the sample of landfill gas comprises adjusting the temperature of the sample of landfill gas using a heating element.

14. The method of claim 10, wherein adjusting the temperature of the sample of landfill gas comprises adjusting the temperature of the sample of landfill gas using a resistive surface configured to generate heat as a result of electric current flowing through the resistive surface.

15. The method of claim 10, wherein the gas characteristic sensor comprises an infrared sensor.

16. The method of claim 10, wherein the gas characteristic sensor comprises an electrochemical sensor.

17. The method of claim 10, wherein obtaining the measurement of the temperature of the sample of landfill gas comprises controlling the temperature sensor to obtain the measurement of the temperature of the sample of landfill gas.

18. The method of claim 10, wherein obtaining the measurement of the temperature of the sample of landfill gas comprises receiving the measurement of the temperature of the sample of landfill gas from at least one second controller configured to control the temperature sensor to obtain the measurement of the temperature of the sample of landfill gas.

19. A control system comprising:
    a chamber;
    a temperature sensor, disposed in the chamber, for measuring temperature of a sample of landfill gas extracted from a landfill;

one or more sensors, disposed in the chamber, for measuring at least one other characteristic of the sample of landfill gas different from the temperature of the sample of landfill gas; and at least one controller configured to perform a method for reducing deterioration of the one or more sensors, the method comprising:

while the sample of landfill gas is in the chamber:

obtaining, from the temperature sensor, a measurement of the temperature of the sample of landfill gas;

responsive to determining, using the measurement of the temperature of the sample of landfill gas, that the temperature of the sample of landfill gas is greater than or equal to a target temperature, operating the one or more sensors to take at least one new measurement of the at least one other characteristic of the sample of landfill gas; and responsive to determining, using the measurement of the temperature of the sample of landfill gas, that the temperature of the sample of landfill gas is not greater than or equal to the target temperature, adjusting the temperature of the sample of landfill gas in the chamber.

20. The control system of claim 19, wherein obtaining the measurement of the temperature of the sample of landfill gas comprises controlling the temperature sensor to obtain the measurement of the temperature of the sample of landfill gas.

\* \* \* \* \*